United States Patent
Cai et al.

(10) Patent No.: US 12,391,653 B2
(45) Date of Patent: Aug. 19, 2025

(54) SALT FORM AND CRYSTAL FORM OF MUTANT IDH1 INHIBITOR AND PREPARATION METHOD THEREFOR

(71) Applicant: KPC PHARMACEUTICALS, INC, Yunnan (CN)

(72) Inventors: Yaxian Cai, Shanghai (CN); Bao Yue, Shanghai (CN); Peng Yu, Shanghai (CN); Changqing Wei, Shanghai (CN); Wenyuan Qian, Shanghai (CN)

(73) Assignee: KPC PHARMACEUTICALS, INC, Yunnan (CN)

( * ) Notice: Subject to any disclaimer, the term of this patent is extended or adjusted under 35 U.S.C. 154(b) by 521 days.

(21) Appl. No.: 17/787,680

(22) PCT Filed: Dec. 22, 2020

(86) PCT No.: PCT/CN2020/138174
§ 371 (c)(1),
(2) Date: Jun. 21, 2022

(87) PCT Pub. No.: WO2021/129587
PCT Pub. Date: Jul. 1, 2021

(65) Prior Publication Data
US 2023/0045991 A1  Feb. 16, 2023

(30) Foreign Application Priority Data
Dec. 23, 2019 (CN) .......................... 201911335601.7

(51) Int. Cl.
*C07D 235/30* (2006.01)

(52) U.S. Cl.
CPC ........ *C07D 235/30* (2013.01); *C07B 2200/13* (2013.01)

(58) Field of Classification Search
CPC ... C07D 235/30; C07B 2200/13; A61P 35/00; A61K 31/4184
See application file for complete search history.

(56) References Cited

U.S. PATENT DOCUMENTS

| | | |
|---|---|---|
| 2017/0197921 A1 | 7/2017 | Rehwinkel et al. |
| 2017/0197922 A1 | 7/2017 | Rehwinkel et al. |
| 2018/0201585 A1 | 7/2018 | Panknin et al. |
| 2018/0215717 A1 | 8/2018 | Panknin et al. |
| 2018/0222870 A1 | 8/2018 | Schirmer |
| 2018/0222871 A1 | 8/2018 | Schirmer |
| 2021/0206728 A1 | 7/2021 | Wang et al. |

FOREIGN PATENT DOCUMENTS

| | | |
|---|---|---|
| CN | 107848985 A | 3/2018 |
| EP | 3816158 A1 | 5/2021 |
| JP | 2017505793 A | 2/2017 |
| JP | 2018521095 A | 8/2018 |
| JP | 2018524371 A | 8/2018 |
| JP | 2018524383 A | 8/2018 |
| WO | 2015/121209 A1 | 8/2015 |
| WO | 2015/121210 A1 | 8/2015 |
| WO | 2017/009325 A1 | 1/2017 |
| WO | 2017/012967 A1 | 1/2017 |
| WO | WO-2020001474 A1 * | 1/2020 ......... A61K 31/4184 |

OTHER PUBLICATIONS

JP Appln. No. 2022-529669 OA dated Jun. 6, 2023.
International Search Report for PCT/CN2020/138174. (Mar. 23, 2021).

(Continued)

*Primary Examiner* — James H Alstrum-Acevedo
*Assistant Examiner* — Pierre Paul Eleniste
(74) *Attorney, Agent, or Firm* — Merchant & Gould P.C.

(57) ABSTRACT

A salt form and crystal form of a mutant IDH1 inhibitor and a preparation method therefor.

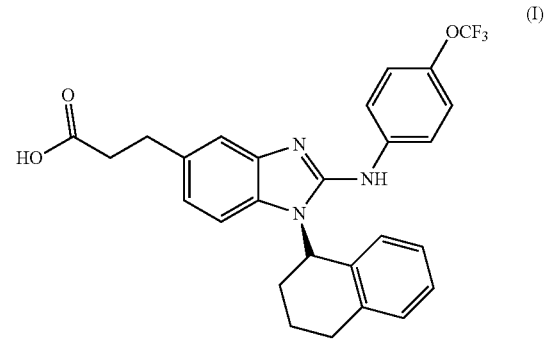

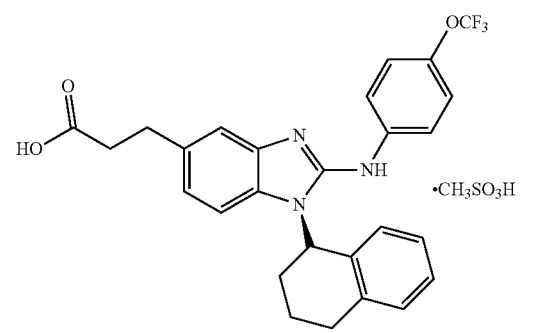

20 Claims, 10 Drawing Sheets

(56) References Cited

OTHER PUBLICATIONS

Hartmann et al., "Type and Frequency of IDH1 and IDH2 mutations are related to astrocytic and oligodendroglial differentiation and age: a study of 1,010 diffuse gliomas", Acta Neuropathologica, 2009, 118(4): 469-474.

Dang et al., "Cancer-associated IDH1 mutations produce 2-hydroxyglutarate", Nature, 2009, 462(7274): 739-744.

Pusch et al., "Pan-mutant IDH1 inhibitor BAY 1436032 for effective treatment of IDH1 mutant astrocytoma in vivo", Acta Neuropathol, 2017, 133(4): 629-644.

Extended European Search Report issued for European Patent Appl. No. 20904644.0 dated Oct. 18, 2023.

Stahl, "Preparation of Water-Soluble Compounds through Salt Formation," The Practice of Medicinal Chemistry, XP-002566271 (2003), 15 pgs.

Caira, "Crystalline Polymorphism of Organic Compounds," Topics in Current Chemistry, vol. 198 (1998), 46 pgs.

\* cited by examiner

SALT FORM AND CRYSTAL FORM OF MUTANT IDH1 INHIBITOR AND PREPARATION METHOD THEREFOR

This application is the national phase of International Application No. PCT/CN2020/138174. titled "SALT FORM AND CRYSTAL FORM OF MUTANT IDH1 INHIBITOR AND PREPARATION METHOD THEREFOR", filed on Dec. 22, 2020, which claims the priority to Chinese Patent Application No. 201911335601.7, titled "SALT FORM AND CRYSTAL FORM OF MUTANT IDHI INHIBITOR AND PREPARATION METHOD THEREFOR", filed on Dec. 23, 2019 with the China National Intellectual Property Administration, which is incorporated herein by reference in entirety.

FIELD

The present disclosure relates to a salt form and crystalline form of a mutant IDHI inhibitor and a preparation method therefor.

BACKGROUND

Isocitrate dehydrogenase, an important enzyme in the citric acid cycle, catalyzes the oxidative decarboxylation of isocitrate to 2-oxoglutaric acid (i.e., 2-α-ketoglutaric acid, α-KG). The gene IDH1 encodes a protein that is an NADP (+)-dependent isocitrate dehydrogenase found in the cytoplasm and peroxisomes, and contains the signal sequence targeting PTS-1 peroxidase. The presence of this enzyme in the peroxisomes suggests a role for internal NADPH regeneration.

Non-mutated such as wild-type IDH catalyzes the oxidative decarboxylation of isocitrate while reducing $NAD^+$ ($NADP^+$) to NADP(NADPH):

$$Isocitrate \pm NA^+(NADP^+) \rightarrow \alpha\text{-}KG \pm CO_2 \pm NADP(NADPH) \pm H^+$$

IDH 1/2 mutant proteins (IDH 1/2 m) have been found in a variety of tumors, including gliomas, acute myeloid leukemia (AML), chondrosarcoma, tumor in intrahepatic bile duct, melanoma, prostate cancer, angioimmunoblastic T-cell lymphoma. Among gliomas, more than 70% of non-primary glioblastomas have IDH1 mutation, and in 92.7% of IDH1-mutated tumors, arginine is substituted by histidine (i.e. IDH1 R132H) (Hartmann C, Acta Neuropathol. 2009 Oct; 1 18(4):469-74).

IDH mutant proteins have a novel protein function, catalyzing the reduction of α-KG to the oncogenic metabolite 2-hydroxyglutaric acid (2-HG). The production of 2-HG is believed to contribute to the formation and progression of cancer (Dang L, Nature, 2009 Dec. 10; 462(7274):739-44). Normal cells produce very low levels of 2-HG, but cells with IDH mutations produce high levels of 2-HG. High levels of 2-HG were also found in tumors with IDH mutations.

Therefore, the inhibition of mutant IDH and its novel activity is a potential approach for cancer therapy, and there is a need for an inhibitor of mutant IDH to inhibit its new role of producing 2-HG.

Acta Neuropathol (2017, Vol(133), Issue 4, 629-644) disclosed the specific structure of compound BAY1436032.

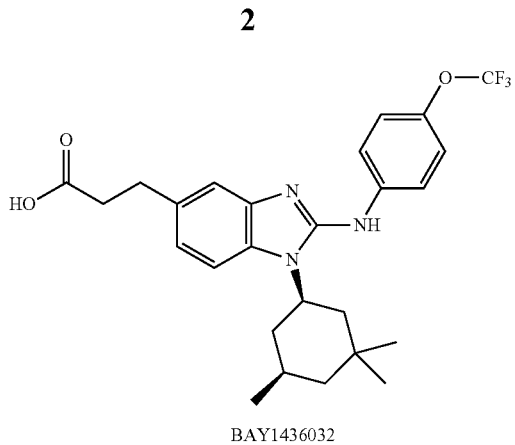

BAY1436032

SUMMARY

The present disclosure provides a crystalline form A of compound represented by formula (I), wherein its X-ray powder diffraction spectrum shows characteristic diffraction peaks at 2 θ angles of 9.78±0.20°, 12.06±0.20° and 20.37±0.20°;

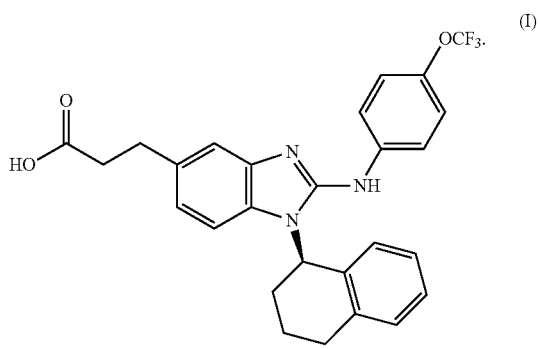 [SMILES: O=C(O)CCc1ccc2c(c1)nc(Nc1ccc(OC(F)(F)F)cc1)n2[C@@H]1CCCc2ccccc21]

(I)

In some embodiments of the present disclosure, the X-ray powder diffraction spectrum of the above-mentioned crystalline form A shows characteristic diffraction peaks at 2 θ angles of 7.66±0.20°, 9.78±0.20°, 12.06±0.20°, 17.43±0.20°, 18.02±0.20°, 18.81±0.20°, 20.37±0.20° and 23.10±0.20°.

In some embodiments of the present disclosure, the X-ray powder diffraction spectrum of the above-mentioned crystalline form A shows characteristic diffraction peaks at 2 θ angles of 7.66±0.20°, 9.78±0.20°, 12.06±0.20°, 17.43±0.20°, 18.02±0.20°, 18.81±0.20°, 20.37±0.20°, 20.91±0.20°, 22.46±0.20° and 23.10±0.20°.

In some embodiments of the present disclosure, the X-ray powder diffraction spectrum of the above-mentioned crystalline form A shows characteristic diffraction peaks at 2 θ angles of 4.88°, 6.03°, 7.66°, 9.78°, 10.57°, 11.65°, 12.06°, 13.13°, 13.55°, 14.70°, 14.94°, 15.34°, 15.73°, 16.02°, 16.64°, 17.43°, 18.02°, 18.34°, 18.81°, 19.25°, 19.60°, 20.37°, 20.91°, 21.17°, 22.03°, 22.46°, 23.10°, 23.68°, 24.25°, 25.16°, 25.51°, 26.44°, 27.14°, 28.77°, 29.42°, 30.97°, 31.76°, 32.29° and 33.16°.

In some embodiments of the present disclosure, the XRPD spectrum of the above-mentioned crystalline form A is shown in FIG. 1.

In some embodiments of the present disclosure, the XRPD spectrum analysis data of the above-mentioned crystalline form A are shown in Table 1:

TABLE 1

XRPD spectrum analysis data of crystalline form A

| No. | 2θ angle (°) | Interplanar spacing (Å) | Relative intensity (%) |
| --- | --- | --- | --- |
| 1 | 4.88 | 18.10 | 3.89 |
| 2 | 6.03 | 14.65 | 4.64 |
| 3 | 7.66 | 11.54 | 53.57 |
| 4 | 9.78 | 9.04 | 79.68 |
| 5 | 10.57 | 8.37 | 10.03 |
| 6 | 11.65 | 7.59 | 13.74 |
| 7 | 12.06 | 7.34 | 100.00 |
| 8 | 13.13 | 6.74 | 4.52 |
| 9 | 13.55 | 6.54 | 5.74 |
| 10 | 14.70 | 6.03 | 11.42 |
| 11 | 14.94 | 5.93 | 14.96 |
| 12 | 15.34 | 5.78 | 12.77 |
| 13 | 15.73 | 5.63 | 18.50 |
| 14 | 16.02 | 5.53 | 12.99 |
| 15 | 16.64 | 5.33 | 4.02 |
| 16 | 17.43 | 5.09 | 33.41 |
| 17 | 18.02 | 4.92 | 33.95 |
| 18 | 18.34 | 4.84 | 29.54 |
| 19 | 18.81 | 4.72 | 45.26 |
| 20 | 19.25 | 4.61 | 5.88 |
| 21 | 19.60 | 4.53 | 6.19 |
| 22 | 20.37 | 4.36 | 85.40 |
| 23 | 20.91 | 4.25 | 24.23 |
| 24 | 21.17 | 4.20 | 17.23 |
| 25 | 22.03 | 4.04 | 9.10 |
| 26 | 22.46 | 3.96 | 23.45 |
| 27 | 23.10 | 3.85 | 40.26 |
| 28 | 23.68 | 3.76 | 13.65 |
| 29 | 24.25 | 3.67 | 9.34 |
| 30 | 25.16 | 3.54 | 9.00 |
| 31 | 25.51 | 3.49 | 22.33 |
| 32 | 26.44 | 3.37 | 18.89 |
| 33 | 27.14 | 3.29 | 5.33 |
| 34 | 28.77 | 3.10 | 7.47 |
| 35 | 29.42 | 3.04 | 2.99 |
| 36 | 30.97 | 2.89 | 4.36 |
| 37 | 31.76 | 2.82 | 13.36 |
| 38 | 32.29 | 2.77 | 3.75 |
| 39 | 33.16 | 2.70 | 2.72 |

In some embodiments of the present disclosure, the differential scanning calorimetry graph of the above-mentioned crystalline form A shows an endothermic peak at 248.7±3.0° C.

In some embodiments of the present disclosure, the DSC graph of the above-mentioned crystalline form A is shown in FIG. 2.

In some embodiments of the present disclosure, the thermogravimetric analysis graph of the above-mentioned crystalline form A has a weight loss of 0.97% at 230.° C.±3.0° C.

In some embodiments of the present disclosure, the TGA graph of the above-mentioned crystalline form A is shown in FIG. 3.

The present disclosure also provides a crystalline form B of compound represented by formula (I), wherein its X-ray powder diffraction spectrum shows characteristic diffraction peaks at 2 θ angles of 11.66±0.20°, 16.69±0.20° and 17.69±0.20°.

In some embodiments of the present disclosure, the X-ray powder diffraction spectrum of the above-mentioned crystalline form B shows characteristic diffraction peaks at 2 θ angles of 7.48±0.20°, 11.66±0.20°, 15.83±0.20°, 16.69±0.20°, 17.69±0.20°, 19.68±0.20°, 21.79±0.20° and 22.90±0.20°.

In some embodiments of the present disclosure, the X-ray powder diffraction spectrum of the above-mentioned crystalline form B shows characteristic diffraction peaks at 2 θ angles of 7.48±0.20°, 11.66±0.20°, 12.47±0.20°, 15.83±0.20°, 16.69±0.20°, 17.69±0.20°, 19.68±0.20°, 21.79±0.20°, 22.90±0.20° and 23.84±0.20°.

In some embodiments of the present disclosure, the X-ray powder diffraction spectrum of the above-mentioned crystalline form B shows characteristic diffraction peaks at 2 θ angles of 7.48°, 11.66°, 12.47°, 14.56°, 15.83°, 16.06°, 16.69°, 17.69°, 18.13°, 19.68°, 21.19°, 21.79°, 22.12°, 22.90°, 23.84°, 25.50° and 29.72°.

In some embodiments of the present disclosure, the XRPD spectrum of the above-mentioned crystalline form B is shown in FIG. 4.

In some embodiments of the present disclosure, the XRPD spectrum analysis data of the above-mentioned crystalline form B are shown in Table 2:

TABLE 2

XRPD spectrum analysis data of crystalline form B

| No. | 2θ angle (°) | Interplanar spacing (Å) | Relative intensity (%) |
| --- | --- | --- | --- |
| 1 | 7.48 | 11.81 | 33.35 |
| 2 | 11.66 | 7.59 | 53.14 |
| 3 | 12.47 | 7.10 | 15.21 |
| 4 | 14.56 | 6.08 | 10.80 |
| 5 | 15.83 | 5.60 | 41.13 |
| 6 | 16.06 | 5.52 | 33.94 |
| 7 | 16.69 | 5.31 | 74.40 |
| 8 | 17.69 | 5.01 | 100.00 |
| 9 | 18.13 | 4.89 | 19.30 |
| 10 | 19.68 | 4.51 | 19.64 |
| 11 | 21.19 | 4.19 | 20.13 |
| 12 | 21.79 | 4.08 | 50.90 |
| 13 | 22.12 | 4.02 | 30.60 |
| 14 | 22.90 | 3.88 | 59.18 |
| 15 | 23.84 | 3.73 | 20.80 |
| 16 | 25.50 | 3.49 | 16.97 |
| 17 | 29.72 | 3.01 | 7.39 |

In some embodiments of the present disclosure, the differential scanning calorimetry graph of the above-mentioned crystalline form B shows an endothermic peak at 246.8±3.0° C.

In some embodiments of the present disclosure, the DSC graph of the above-mentioned crystalline form B is shown in FIG. 5.

In some embodiments of the present disclosure, the thermogravimetric analysis graph of the above-mentioned crystalline form B shows a weight loss of 0.54% at 230.0° C.±3.0° C.

In some embodiments of the present disclosure, the TGA graph of the above-mentioned crystalline form B is shown in FIG. 6.

The present disclosure also provides a crystalline form C of compound represented by formula (I), wherein its X-ray powder diffraction spectrum shows characteristic diffraction peaks at 2 θ angles of 9.59±0.20°, 18.19±0.20° and 19.74±0.20°.

In some embodiments of the present disclosure, the X-ray powder diffraction spectrum of the above-mentioned crystalline form C shows characteristic diffraction peaks at 2 θ angles of 9.59±0.20°, 12.17±0.20°, 12.65±0.20°, 18.19±0.20°, 18.87±0.20°, 19.74±0.20°, 21.27±0.20° and 23.05±0.20°.

In some embodiments of the present disclosure, the X-ray powder diffraction spectrum of the above-mentioned crystalline form C shows characteristic diffraction peaks at 2 θ angles of 9.59±0.20°, 11.60±0.20°, 12.17±0.20°, 12.65±0.20°, 18.19±0.20°, 18.87±0.20°, 19.74±0.20°, 21.27±0.20°, 22.20±0.20° and 23.05±0.20°.

In some embodiments of the present disclosure, the X-ray powder diffraction spectrum of the above-mentioned crystalline form C shows characteristic diffraction peaks at 2 θ angles of 7.70°, 9.59°, 10.78°, 11.60°, 12.17°, 12.65°, 17.70°, 18.19°, 18.87°, 19.74°, 20.12°, 21.27°, 22.20°, 23.05°, 25.25°, 25.61°, 26.43° and 28.53°.

In some embodiments of the present disclosure, the XRPD spectrum of the above-mentioned crystalline form C is shown in FIG. 7.

In some embodiments of the present disclosure, the XRPD spectrum analysis data of the above-mentioned crystalline form C are shown in Table 3:

TABLE 3

XRPD spectrum analysis data of crystalline form C

| No. | 2θ angle (°) | Interplanar spacing (Å) | Relative intensity (%) |
|---|---|---|---|
| 1 | 7.70 | 11.48 | 15.29 |
| 2 | 9.59 | 9.22 | 78.12 |
| 3 | 10.78 | 8.21 | 12.99 |
| 4 | 11.60 | 7.63 | 32.92 |
| 5 | 12.17 | 7.27 | 44.74 |
| 6 | 12.65 | 7.00 | 36.00 |
| 7 | 17.70 | 5.01 | 35.00 |
| 8 | 18.19 | 4.88 | 73.95 |
| 9 | 18.87 | 4.70 | 62.27 |
| 10 | 19.74 | 4.50 | 100.00 |
| 11 | 20.12 | 4.41 | 74.47 |
| 12 | 21.27 | 4.18 | 44.81 |
| 13 | 22.20 | 4.00 | 34.67 |
| 14 | 23.05 | 3.86 | 61.51 |
| 15 | 25.25 | 3.53 | 8.04 |
| 16 | 25.61 | 3.48 | 20.01 |
| 17 | 26.43 | 3.37 | 12.60 |
| 18 | 28.53 | 3.13 | 8.18 |

In some embodiments of the present disclosure, the differential scanning calorimetry graph of the above-mentioned crystalline form C shows an endothermic peak at 248.6±3.0° C.

In some embodiments of the present disclosure, the DSC graph of the above-mentioned crystalline form C is shown in FIG. 8.

In some embodiments of the present disclosure, the thermogravimetric analysis graph of the above-mentioned crystalline form C shows a weight loss of 3.01% at 230.0° C.±3.0° C.

In some embodiments of the present disclosure, the TGA graph of the above-mentioned crystalline form C is shown in FIG. 9.

The present disclosure also provides a compound represented by formula (II),

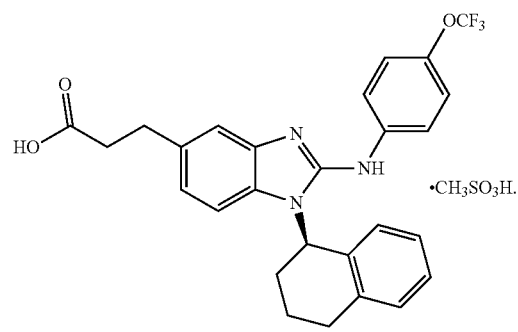

(II)

The present disclosure also provides a crystalline form D of the compound represented by formula (II), wherein its X-ray powder diffraction spectrum shows characteristic diffraction peaks at 2 θ angles of 16.85°±0.20°, 19.93°±0.20° and 21.89°±0.20°.

In some embodiments of the present disclosure, the X-ray powder diffraction spectrum of the above-mentioned crystalline form D shows characteristic diffraction peaks at 2 θ angles of 7.31±0.20°, 8.48±0.20°, 13.08±0.20°, 16.85±0.20°, 17.44±0.20°, 19.93±0.20°, 21.89±0.20° and 22.49±0.20°.

In some embodiments of the present disclosure, the X-ray powder diffraction spectrum of the above-mentioned crystalline form D shows characteristic diffraction peaks at 2 θ angles of 7.31°, 8.48°, 13.08°, 14.64°, 16.85°, 17.44°, 19.93°, 21.89°, 22.49° and 25.87°.

In some embodiments of the present disclosure, the XRPD spectrum of the above-mentioned crystalline form D is shown in FIG. 10.

In some embodiments of the present disclosure, the XRPD spectrum analysis data of the above-mentioned crystalline form D are shown in Table 4:

TABLE 4

XRPD spectrum analysis data of crystalline form D

| No. | 2θ angle (°) | Interplanar spacing (Å) | Relative intensity (%) |
|---|---|---|---|
| 1 | 7.31 | 12.10 | 26.38 |
| 2 | 8.48 | 10.42 | 17.84 |
| 3 | 13.08 | 6.77 | 22.72 |
| 4 | 14.64 | 6.05 | 12.26 |
| 5 | 16.85 | 5.26 | 100.00 |
| 6 | 17.44 | 5.08 | 25.53 |
| 7 | 19.93 | 4.45 | 35.16 |
| 8 | 21.89 | 4.06 | 73.11 |
| 9 | 22.49 | 3.95 | 22.07 |
| 10 | 25.87 | 3.44 | 17.44 |

In some embodiments of the present disclosure, the differential scanning calorimetry graph of the above-mentioned crystalline form D shows an endothermic peak at 211.6±3.0° C.

In some embodiments of the present disclosure, the DSC graph of the above-mentioned crystalline form D is shown in is shown in FIG. 11.

In some embodiments of the present disclosure, the thermogravimetric analysis graph of the above-mentioned crystalline form D shows a weight loss of 2.50% at 210.0° C.±3.0° C.

In some embodiments of the present disclosure, the TGA graph of the above-mentioned crystalline form D is shown in FIG. 12.

The present disclosure also provides a compound represented by formula (III),

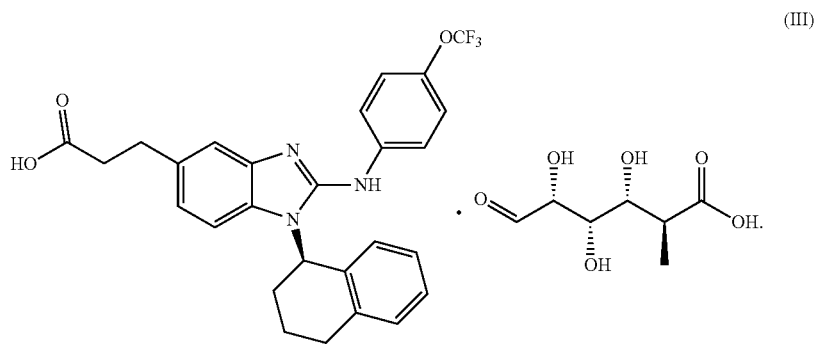 [SMILES: O=C(O)CCc1ccc2c(c1)nc(Nc1ccc(OC(F)(F)F)cc1)n2[C@@H]1CCCc2ccccc21 ; C[C@H](C(=O)O)[C@@H](O)[C@H](O)[C@@H](O)C=O]

(III)

The present disclosure also provides a crystalline form E of the compound represented by formula (III), wherein its X-ray powder diffraction spectrum shows characteristic diffraction peaks at 2 θ angles of 15.07°±0.20°, 20.07°±0.20° and 25.50°±0.20°.

In some embodiments of the present disclosure, the X-ray powder diffraction spectrum of the above-mentioned crystalline form E shows characteristic diffraction peaks at 2 θ angles of 11.80±0.20°, 15.07±0.20°, 17.71±0.20°, 20.07±0.20°, 22.54±0.20°, 24.42±0.20°, 25.50±0.20° and 26.20±0.20°.

In some embodiments of the present disclosure, the X-ray powder diffraction spectrum of the above-mentioned crystalline form E shows characteristic diffraction peaks at 2 θ angles of 11.10°, 11.80°, 15.07°, 16.70°, 17.71°, 20.07°, 20.48°, 22.54°, 24.42°, 25.50°, 26.20°, 28.99°, 30.63°, 35.34°, 38.41° and 39.31°.

In some embodiments of the present disclosure, the XRPD spectrum of the above-mentioned crystalline form E is shown in FIG. 13.

In some embodiments of the present disclosure, the XRPD spectrum analysis data of the above-mentioned crystalline form E are as shown in Table 5:

TABLE 5

XRPD spectrum analysis data of crystalline form E

| No. | 2θ angle (°) | Interplanar spacing (Å) | Relative intensity (%) |
|---|---|---|---|
| 1 | 11.10 | 7.97 | 30.29 |
| 2 | 11.80 | 7.50 | 31.99 |
| 3 | 15.07 | 5.88 | 96.50 |
| 4 | 16.70 | 5.31 | 14.65 |
| 5 | 17.71 | 5.01 | 29.15 |
| 6 | 20.07 | 4.42 | 100.00 |
| 7 | 20.48 | 4.34 | 31.37 |
| 8 | 22.54 | 3.94 | 35.07 |
| 9 | 24.42 | 3.64 | 42.24 |
| 10 | 25.50 | 3.49 | 57.28 |
| 11 | 26.20 | 3.40 | 37.68 |
| 12 | 28.99 | 3.08 | 7.68 |
| 13 | 30.63 | 2.92 | 41.56 |
| 14 | 35.34 | 2.54 | 27.95 |
| 15 | 38.41 | 2.34 | 17.36 |
| 16 | 39.31 | 2.29 | 17.16 |

In some embodiments of the present disclosure, the differential scanning calorimetry graph of the above-mentioned crystalline form E shows endothermic peaks at 163.5±3.0° C. and 240.4±3.0° C., respectively.

In some embodiments of the present disclosure, the DSC graph of the above-mentioned crystalline form E is shown in FIG. 14.

In some embodiments of the present disclosure, the thermogravimetric analysis graph of the above-mentioned crystalline form E shows a weight loss of 0.29% at 140.0° C.±3.0° C.

In some embodiments of the present disclosure, the TGA graph of the above-mentioned crystalline form E is shown in FIG. 15.

The present disclosure also provides a compound represented by formula (IV),

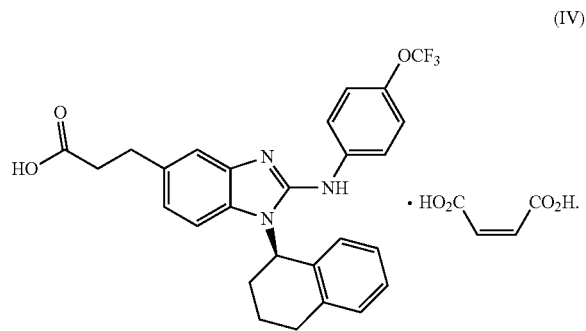 [SMILES: O=C(O)CCc1ccc2c(c1)nc(Nc1ccc(OC(F)(F)F)cc1)n2[C@@H]1CCCc2ccccc21 ; O=C(O)/C=C\C(=O)O]

(IV)

The present disclosure also provides a crystalline form F of the compound represented by formula (IV), wherein its X-ray powder diffraction spectrum shows characteristic diffraction peaks at 2 θ angles of 8.19°±0.20°, 11.11°±0.20° and 22.37°±0.20°.

In some embodiments of the present disclosure, the X-ray powder diffraction spectrum of the above-mentioned crystalline form F shows characteristic diffraction peaks at 2 θ angles of 8.19±0.20°, 11.11±0.20°, 15.74±0.20°, 17.12±0.20°, 18.16±0.20°, 21.78±0.20°, 22.37±0.20° and 23.86±0.20°.

In some embodiments of the present disclosure, the X-ray powder diffraction spectrum of the above-mentioned crystalline form F shows characteristic diffraction peaks at 2 θ angles of 8.19°, 8.53°, 11.11°, 15.74°, 17.12°, 18.16°, 18.95°, 19.50°, 21.12°, 21.78°, 22.37°, 22.77°, 23.86° and 25.66°.

In some embodiments of the present disclosure, the XRPD spectrum of the above-mentioned crystalline form F is shown in FIG. 16.

In some embodiments of the present disclosure, the XRPD spectrum analysis data of the above-mentioned crystalline form F are shown in Table 6:

TABLE 6

XRPD spectrum analysis data of crystalline form F

| No. | 2θ angle (°) | Interplanar spacing (Å) | Relative intensity (%) |
|---|---|---|---|
| 1 | 8.19 | 10.80 | 80.08 |
| 2 | 8.53 | 10.36 | 29.09 |
| 3 | 11.11 | 7.97 | 46.45 |
| 4 | 15.74 | 5.63 | 45.90 |
| 5 | 17.12 | 5.18 | 41.81 |
| 6 | 18.16 | 4.88 | 38.42 |
| 7 | 18.95 | 4.68 | 25.38 |
| 8 | 19.50 | 4.55 | 20.42 |
| 9 | 21.12 | 4.21 | 19.77 |
| 10 | 21.78 | 4.08 | 48.01 |
| 11 | 22.37 | 3.98 | 100.00 |
| 12 | 22.77 | 3.91 | 63.35 |
| 13 | 23.86 | 3.73 | 27.01 |
| 14 | 25.66 | 3.47 | 19.37 |

In some embodiments of the present disclosure, the differential scanning calorimetry graph of the above-mentioned crystalline form F shows an endothermic peak at 141.5±3.0° C.

In some embodiments of the present disclosure, the DSC graph of the above-mentioned crystalline form F is shown in FIG. 17.

In some embodiments of the present disclosure, the thermogravimetric analysis graph of the above-mentioned crystalline form F shows a weight loss of 1.08% at 130.0° C.±3.0° C.

In some embodiments of the present disclosure, the TGA graph of the above-mentioned crystalline form F is shown in FIG. 18.

The present disclosure also provides use of the above-mentioned compound, crystalline form A, crystallineline form B, crystalline form C, crystalline form D, crystalline form E or crystalline form F in the manufacture of a medicament for treating tumor in intrahepatic bile duct and the like.

Technical Effect

Each crystalline form of the compound of the present disclosure has the advantages of good stability, good hygroscopicity and little influence by light and heat, and has a broad prospect for medicine. The compound represented by formula (I) has a good inhibitory effect on mutant IDH1R132H and IDH1R132C at the enzymatic level, and has no inhibitory effect on wild-type IDH protein. At the cellular level, the compound represented by formula (I) has a good 2-HG inhibitory effect on U87MG glioma cells with IDH1R132H mutation. The compound represented by formula (I) has good pharmacokinetic properties in mice.

Definition and Explanation

Unless otherwise specified, the following terms and phrases used herein are intended to have the following meanings. A particular phrase or term should not be considered indeterminate or unclear without a specific definition, but should be understood in its ordinary meaning. When a trade name appears herein, it is intended to refer to its corresponding commercial product or its active ingredient.

The intermediate compounds of the present disclosure can be prepared by a variety of synthetic methods well known to those skilled in the art, including the specific embodiments listed below, the embodiments formed by their combination with other chemical synthesis methods, and equivalent alternatives well known to those skilled in the art. The preferred embodiments include, but are not limited to, the examples of the present disclosure.

The chemical reactions of specific embodiments of the present disclosure are carried out in appropriate solvents suitable for the chemical changes of the present disclosure and their required reagents and materials. In order to obtain the compounds of the present disclosure, it is sometimes necessary for those skilled in the art to modify or select the synthetic steps or reaction schemes on the basis of the existing embodiments.

The present disclosure will be specifically described below by means of examples, which do not imply any limitation of the present disclosure.

All solvents used in the present disclosure are commercially available and used without further purification.

The solvents used in the present disclosure are commercially available. The following abbreviations are used in the present disclosure: EtOH represents ethanol; MeOH represents methanol; EtOAc represents ethyl acetate; TFA represents trifluoroacetic acid; TsOH represents p-toluenesulfonic acid; mp represents melting point; THF represents tetrahydrofuran; $K_2CO_3$ represents potassium carbonate; NaOH represents sodium hydroxide; DMSO represents dimethyl sulfoxide; $MeSO_3H$ represents methanesulfonic acid; and EDCI represents 1-(3-dimethylaminopropyl)-3-ethylcarbodiimide hydrochloride.

Compounds are named according to conventional nomenclature in the art or using ChemDraw® software, and commercially available compounds use their supplier catalog names.

X-ray powder diffraction (XRPD) method of the present disclosure

Instrument model: X'Pert3 X-ray diffractometer from PANalytical

Test Method: Approximately 10 mg of sample was used for XRPD detection.

The detailed XRPD parameters were as follows:
Radiation source: Cu, kα (Kα1±1.540598 Å, Kα2±1.544426 Å, intensity ratio of Kα2/Kα1: 0.5)
Light tube voltage: 45 kV, light tube current: 40 mA
Divergence slit: fixed ⅛ deg
$1^{st}$ Soller Slit: 0.04 rad, $2^{nd}$ Soller Slit: 0.04 rad
Receiving slit: None, Anti-scatter slit: 7.5 mm
Measurement time: 5 min
Scanning angle range: 3-40 deg
Step width angle: 0.0263 deg
Step size: 46.665 s
Rotational speed of sample tray: 15 rpm Differential scanning calorimetry (DSC) method of the present disclosure Instrument model: TA DiscoveryDSC2500 Differential Scanning calorimeter.

Test method: The sample (1-10 mg) was placed in a covered aluminum crucible, and heated from room temperature to 300° C. (or 350° C.) at a heating rate of 10° C./min under the protection of 50 mL/min dry $N_2$, while the heat change of the sample during the heating process was recorded by the TA software.

Thermal gravimetric analysis (TGA) method of the present disclosure

Instrument model: TADiscoveryTGA 5500 thermal gravimetric analyzer

Test method: The sample (2-15 mg) was placed in a platinum crucible, and heated from room temperature to 350° C. at a heating rate of 10° C./min under the protection of 50 mL/min dry $N_2$ using the method of segmented high-resolution detection, while the weight change of the sample during the heating process was recorded by the TA software.

Dynamic Vapor Sorption (DVS) Method of the Present Disclosure

Instrument model: SMS DVS intrinsic dynamic moisture adsorption instrument

Test conditions: 10 mg of the sample was weighed out and placed in a DVS sample tray for testing.

The detailed DVS parameters were as follows:
Temperature: 25° C.
Balance: dm/dt±0.01%/min
Drying: 120 min at 0% RH
RH (%) test gradient: 5%
RH (%) test gradient range: 0%-95%-0%
The hygroscopicity evaluation is classified as follows:

| Hygroscopic classification | Moisture adsorption standard (ΔW %) |
|---|---|
| Deliquescent | Adsorbing enough moisture to form a liquid |
| Very hygroscopic | ΔW % ≥ 15% |
| Hygroscopic | 15% > ΔW % ≥ 2% |
| Slightly hygroscopic | 2% > ΔW % ≥ 0.2% |
| Non-hygroscopic | ΔW % < 0.2% |

Note:
ΔW % represents the hygroscopic weight gain of the test article at 25 ± 1° C. and 80 ± 2% RH (European Pharmacopoeia 6.0)

DETAILED DESCRIPTION

Figure 1:
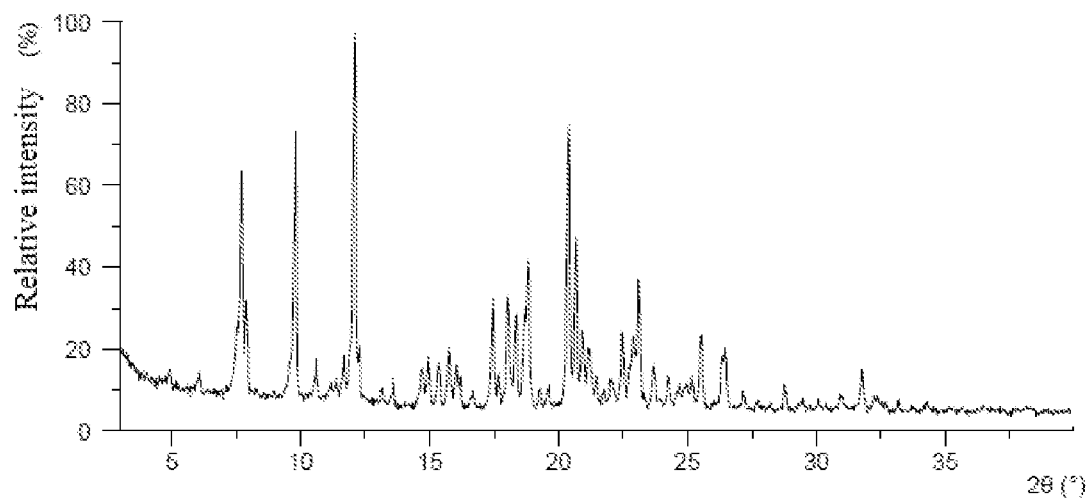
FIG. 1 is the Cu-Kα-radiated XRPD spectrum of the crystalline form A of compound represented by formula (I)
Figure 2:
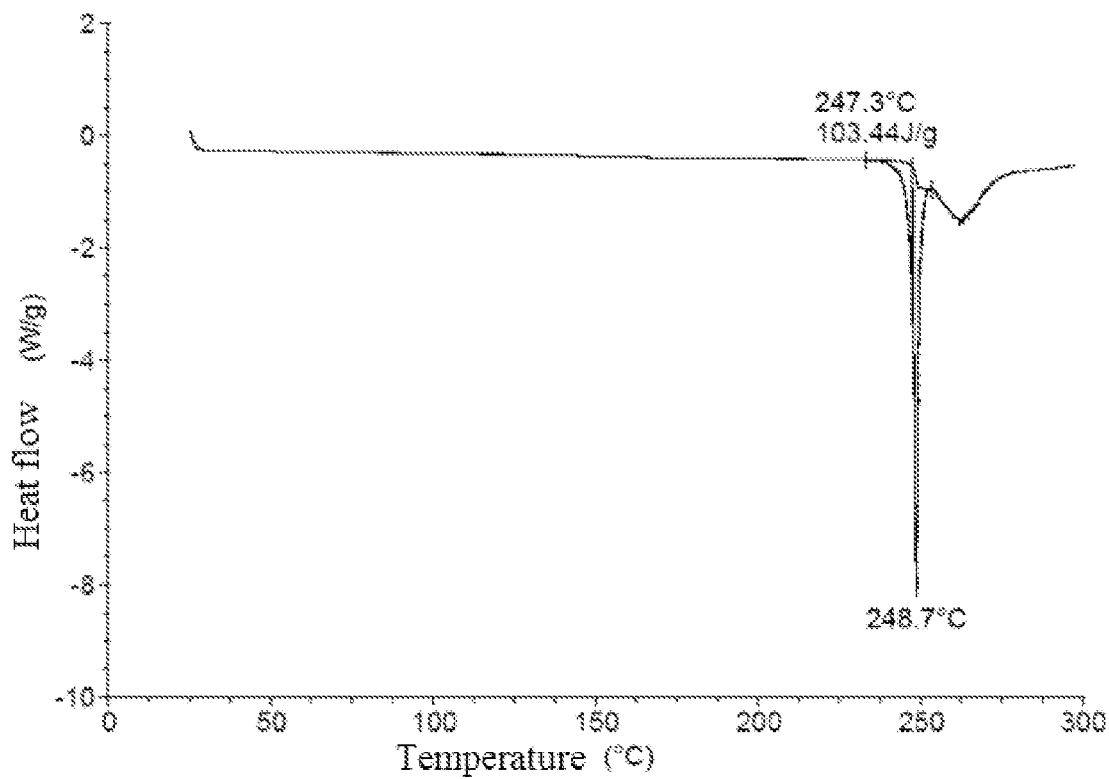
FIG. 2 is the DSC graph of the crystalline form A of compound represented by formula (I)
Figure 3:
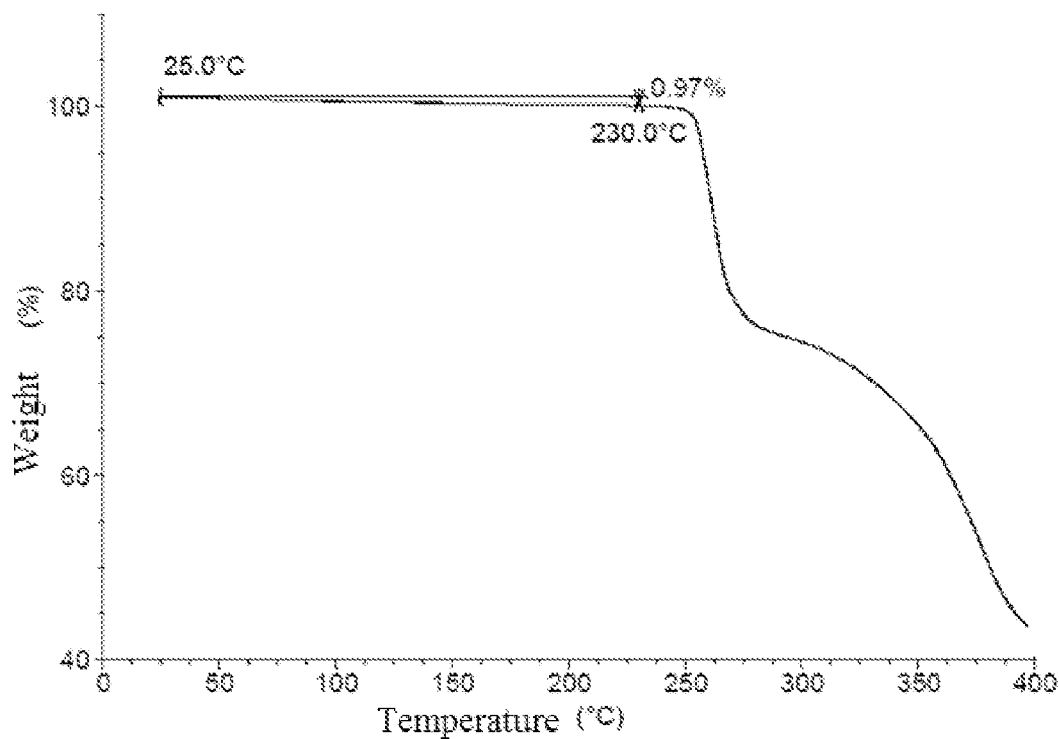
FIG. 3 is the TGA graph of the crystalline form A of compound represented by formula (I)

In order to better understand the content of the present disclosure, it will be further illustrated below in conjunction with specific examples, but the specific examples do not limit the content of the present disclosure.

Example 1

Preparation of Compound Represented by Formula (I)

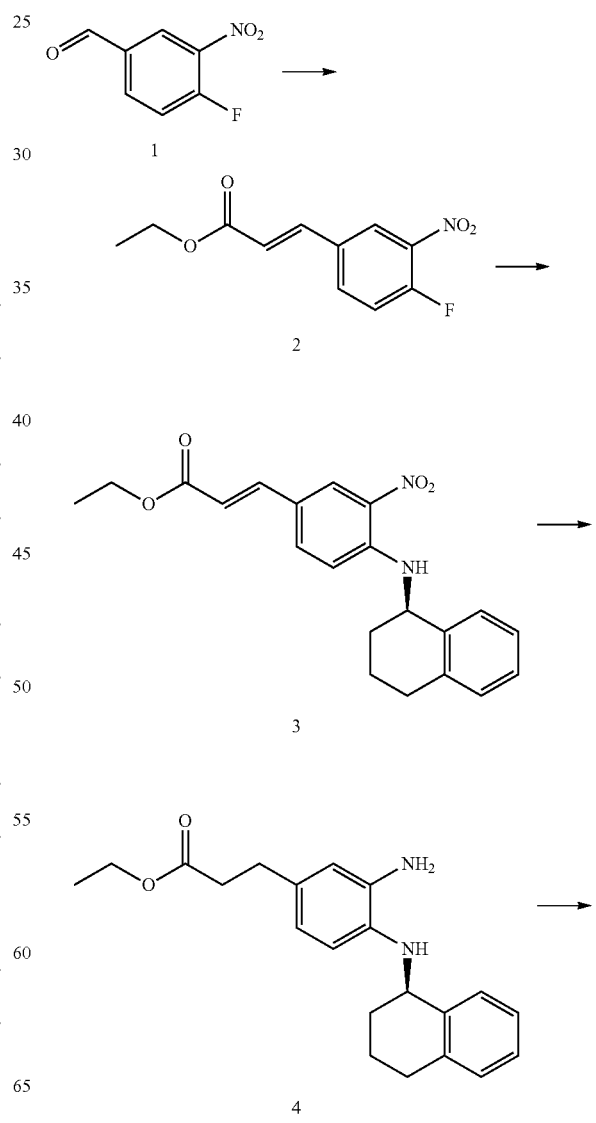

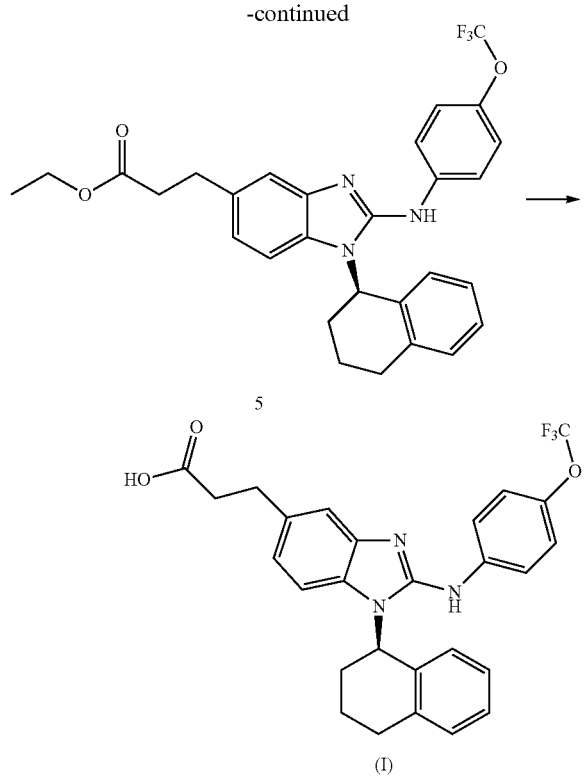

Step 1:

THF (4.05 L) was added at one time to a 50 L high-low temperature reaction kettle and the internal temperature was controlled at 20~30° C. Compound 1 (1345.47 g, 7.91 mol) was added, followed by triethyl phosphoryl acetate (1912.00 g, 8.36 mol). The internal temperature was controlled, and the prepared aqueous $K_2CO_3$ solution (3.97 L, 4 M) was added dropwise. After the addition, the system was stirred at 20-30° C. for 17 h and then the reaction was terminated. Water (12 L) was added to the reaction kettle and stirred for 2 h. The system was filtered, and the filter cake was rinsed with water (5 L) and dried under vacuum (−0.1 Mpa, 50° C.) to obtain compound 2.

Step 2:

Ethyl acetate (4.55 L) and n-hexane (4.55 L) were added to a 50 L high-low temperature reaction kettle and the internal temperature was controlled at 30~40° C. Then compound 2 (1710.00 g, 7.15 mol) was added, followed by $K_2CO_3$ (1001.00 g, 7.17 mol) and (R)-1,2,3,4-tetrahydro-1-naphthylamine (1111.50 g, 7.49 mol), and the internal temperature was controlled to 70~80° C. The system was stirred for 16 h and the reaction was terminated. The internal temperature was controlled at 70~75° C., and the system was released into three 5L barrels under stirring and cooled to 30~40° C. naturally to precipitate a large amount of solid, which was triturated to obtain a crude product. N-hexane (17 L) and water (5.1 L) were added to the reaction kettle and the internal temperature was controlled to 30~40° C. The above crude product was added and stirred for 4 h. After filtration, the filter cake was rinsed with a mixed solvent of n-hexane (5 L) and water (5 L), sucked and dried under vacuum −0.1 Mpa, 50° C.) to obtain compound 3.

Step 3:

Compound 3 (500.00 g, 1.36 mol), wet palladium carbon (50 g, 10% content) and THF (5L) were added to a 10L autoclave. The system was replaced with argon three times followed by hydrogen three times, introduced with hydrogen (2.8 Mpa) and stirred at 25~35° C. for 1 h. The system was supplemented with hydrogen to 2.8 Mpa and continued to be stirred for 1 h. Then the system was supplemented with hydrogen to 2.8 Mpa again and stirred for 16.5 h, and the reaction was terminated. The reaction solution was filtered through a celite layer. The filtrate was collected. The filter cake was rinsed twice with THF (500 mL*2), and the filtrate was combined for about 6 L. The filtrate containing compound 4 was directly used in the next step, and the yield was calculated as theoretical 100%.

Step 4:

Compound 4 (1837.36 g, 5.43 mol, 18.5 L of the THF solution) was added at one time to a 50 L high-low temperature reaction kettle and the internal temperature was controlled at 20~30° C. Then 4-trifluoromethoxy phenyl isothiocyanate (1194.00 g, 5.45 mol) was added, heated to 40~45° C. and stirred for 1 h. Then EDCI (1150.00 g, 6.00 mol) was added, heated to 65~70° C. and stirred for 17 h. The reaction system was cooled to 30~40° C. and filtered, and the filtrate was collected. The filtrate was concentrated (−0.1 MPa, 50° C.) to obtain compound 5, which was directly used in the next step, and the yield was calculated as theoretical 100%.

Step 5:

Compound 5 (2832.31 g, 5.41 mol) and EtOH (11.37 L) were added to a 50 L high-low temperature reaction kettle in sequence. NaOH (437.13 g, 10.93 mol) was dissolved in water (5.65 L) and the mixture was slowly added dropwise to the kettle with the dripping speed controlled according to the temperature change, and the internal temperature was controlled to 25~35° C. After the addition, the system was stirred at 25~35° C. for 16 h and then the reaction was terminated. Dilute hydrochloric acid (1M) was lowly added dropwise to the system to adjust pH±5-6, with about 11 L of dilute hydrochloric acid consumed. After the adjustment, the system was continued to be stirred at 25~35° C. for 2 h, then filtered and sucked. The filter cake was washed with a mixed solvent of EtOH and water (EtOH: water ±1:1, 5.6 L) and sucked. The obtained filter cake was dried under reduced pressure (−0.1 MPa, 50° C.) to obtain compound represented by formula (I). $^1$H NMR (400 MHz, $CD_3OD$) δ 7.60 (d, J±8.6 Hz, 2H), 7.33-7.15 (m, 5H), 7.04 (br t, J±7.0 Hz, 1H), 6.83 (br d, J±7.6 Hz, 1H), 6.74 (br d, J±7.9 Hz, 1H), 6.41 (br d, J±8.1 Hz, 1H), 5.88 (br t, J±8.1 Hz, 1H), 3.15-3.01 (m, 1H), 3.00-2.85 (m, 3H), 2.57 (br t, J±7.4 Hz, 2H), 2.30 (br s, 2H), 2.13 (br s, 1H), 2.01 (br d, J±16.1 Hz, 1H).

Example 2

Preparation of Crystalline Form A of Compound Represented by Formula (I)

The compound represented by formula (I) (360 g) was dissolved in DMSO (400 mL) and heated to 80° C. Under stirring, a mixed solution of EtOH (2480 mL) and water (1080 mL) was added dropwise to the solution. The dropwise addition was completed after about 2 h, and then the heating was stopped. The solution was cooled slowly to 20° C., continued to be stirred for 58 h and then filtered. The obtained filter cake was soaked in EtOH (500 mL) for 10 min, filtered and sucked. The procedure was repeated three times. The filter cake was collected and dried to constant weight under vacuum to obtain crystalline form A of the compound represented by formula (I).

Example 3

Preparation of Crystalline Form B of Compound Represented by Formula (I)

The crystalline form A of the compound represented by formula (I) (20 mg) was added to a reaction flask, and acetone (0.3 mL) was added to form a suspension. The suspension was magnetically stirred at room temperature for 6 days, centrifuged and removed of the supernatant. Solid was dried under vacuum at 50° C. for two hours to obtain crystalline form B of the compound represented by formula (I).

The crystalline form A of the compound represented by formula (I) (20 mg) was added to a reaction flask, and ethyl acetate (0.3 mL) was added to form a suspension. The suspension was magnetically stirred at room temperature for 6 days, centrifuged and removed of the supernatant. Solid was dried under vacuum at 50° C. for two hours to obtain crystalline form B of the compound represented by formula (I).

Example 4

Preparation of Crystalline Form B of Compound Represented by Formula (I)

EtOH (7344 mL), DMSO (1836 mL) and the compound represented by formula (I) (2295.00 g, 4.63 mol) were added to a 50 L high-low temperature reaction kettle in sequence. After the addition, the internal temperature was controlled at 80-85° C. to achieve complete dissolution. Then the system was filtered while hot to remove insoluble impurities. The filtrate was poured into the kettle again, and the temperature in the kettle was controlled at 82° C. After the temperature was stable, a mixed solution of EtOH: water±2:1 was slowly added dropwise to the system, and the situation in the kettle was observed during the dropwise addition. When the phenomenon of slight turbidity and then rapid dissolving during the dropwise addition appeared (the temperature at this time was 78° C., and 1200 mL of solvent was consumed), 6 g of crystalline form B of the compound represented by formula (I) was added to the system in batches as a seed crystal. After the seed crystal was added, the system became turbid, and then heating was stopped. The system was naturally cooled to 25-35° C. and stirred for 16.5 h. The temperature was controlled at 25-35° C., and 17160 mL of a mixed solution of EtOH: water±2:1 was slowly added dropwise into the system. After the dropwise addition, the system was continued to be stirred at 25-35° C. and stopped after a total of 24 h of stirring, then filtered and sucked. The filter cake was washed with a solvent of EtOH: water±2:1 (5L*2), and sucked. The obtained solid was added to the reaction kettle, added with EtOH (5.5 L). The mixture was stirred at 25-35° C. for 1.5 h, which was then stopped, and then filtered and sucked. The filter cake was dried under vacuum at 50° C. to constant weight to obtain crystalline form B of the compound represented by formula (I).

Example 5

Preparation of Crystalline Form C of Compound Represented by Formula (I)

The crystalline form A of the compound represented by formula (I) (20 mg) was added to a reaction flask, and THF (0.3 mL) was added to form a suspension. The suspension was magnetically stirred at room temperature for 6 days, and n-hexane was added dropwise until insoluble matter was precipitated. The system was centrifuged and removed of the supernatant. Solid was dried under vacuum at 50° C. for two hours to obtain crystalline form C of the compound represented by formula (I).

Example 6

Preparation of Crystalline Form D of Compound Represented by Formula (II)

The crystalline form A of the compound represented by formula (I) (20 mg) was added to a reaction flask, and acetone (0.3 mL) containing MeSO~3H (3 µL) was added. The system was magnetically stirred at room temperature for 5 days, centrifuged and removed of the supernatant. Solid was dried under vacuum at 50° C. for two hours to obtain crystalline form D of the compound represented by formula (II).

Example 7

Preparation of Crystalline Form E of Compound Represented by Formula (III)

The crystalline form A of the compound represented by formula (I) (20 mg) and D-glucuronic acid (8.5 mg) were added to a reaction flask, and acetone (0.3 mL) was added. The system was magnetically stirred at room temperature for 5 days, centrifuged and removed of the supernatant. Solid was dried under vacuum at 50° C. for two hours to obtain crystalline form E of the compound represented by formula (III).

Example 8

Preparation of Crystalline Form F of compound represented by formula (IV)

The crystalline form A of the compound represented by formula (I) (20 mg) and maleic acid (5.1 mg) were added to a reaction flask, and ethyl acetate (0.3 mL) was added. The system was magnetically stirred at room temperature for 5 days, and n-heptane was added until solid was precipitated. After centrifugation, the filter cake was collected and dried under vacuum at 50° C. for two hours to obtain crystalline form F of compound represented by formula (IV).

Example 9

Study on Hygroscopicity of Crystalline Form B of Compound Represented by Formula (I)

Figure 19:
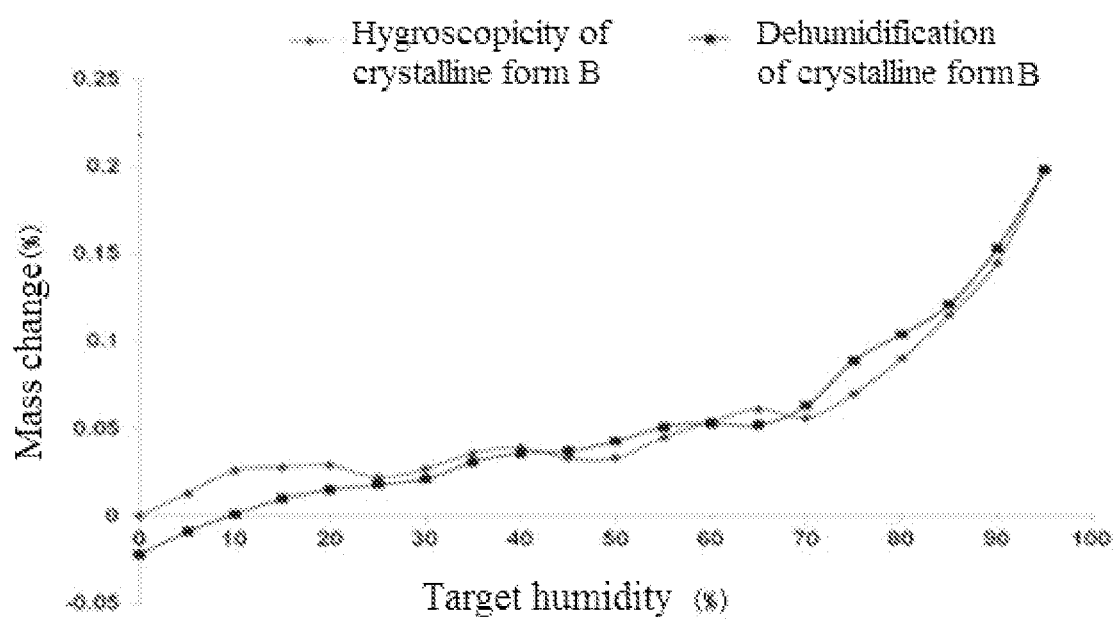
FIG. 19 is the DVS graph of the crystalline form B of compound represented by formula (I).

Experimental Materials:
  SMS DVS intrinsic Dynamic Vapor Sorption Instrument
Experimental Method:
  10.03 mg of crystalline form B of the compound represented by formula (I) was weighed out and placed in a DVS sample tray for testing.
Experimental Results:
  The DVS graph of the crystalline form B of the compound represented by formula (I) is shown in FIG. 19, ΔW±0.09%.
Experimental Conclusions:
  The hygroscopic weight gain of the crystalline form B of the compound represented by formula (I) at 25° C. and 80% RH was 0.09%, indicating it was non-hygroscopic.

Example 10

Solid Stability Test of Crystalline Form B of Compound Represented by Formula (I)

According to the "Guidelines for Stability Test of Raw Materials and Preparations" (General Principles 9001 of Part Four of Chinese Pharmacopoeia 2015 Edition), crystalline form E of the compound represented by formula (I) was investigated for stability at high temperature (60° C., open), high humidity (room temperature/relative humidity 92.5%, open) and strong light (5000 lx, closed).

About 10 mg of compound represented by formula (I) was accurately weighed out, placed in a dry and clean glass bottle, spread out into a thin layer and covered with aluminum foil with small holes under the influence factor test conditions (60° C., 92.5% RH) and accelerated conditions (40° C./75% RH and 60° C./75% RH). The samples placed under the condition of light (visible light 1200000 Lux, ultraviolet 200 W) were in transparent glass bottles, with one group fully exposed and the other fully packaged with aluminum foil. Samples in duplicate were placed under each condition at each time point, and the samples for XRPD detection were placed separately. Samples placed under different conditions were sampled for XRPD detection at the planned test end point, and the test results were compared with the initial test results at Day 0. The test results are shown in Table 7 below:

TABLE 7

Solid stability test results of crystalline form B of compound represented by formula (I)

| Test condition | Time point | Crystalline form |
|---|---|---|
| — | 0 days | Crystalline form B |
| 60° C., open | 5 days | Crystalline form B |
|  | 10 days | Crystalline form B |
| 25° C./92.5% RH, open | 5 days | Crystalline form B |
|  | 10 days | Crystalline form B |
| Light (total illuminance = 1.2 × 10⁶ Lux2 × 10, Near UV = 200 w · hr/m², open) | 5 days | Crystalline form B |
|  | 10 days | Crystalline form B |
| 40° C./75% RH, open | 1 month | Crystalline form B |
|  | 2 months | Crystalline form B |
|  | 3 months | Crystalline form B |
| 60° C./75% RH, open | 1 month | Crystalline form B |
|  | 2 months | Crystalline form B |

Conclusion: The crystalline form B of compound represented by formula (I) had good stability under conditions of high temperature, high humidity and strong light and accelerated conditions. Experimental example 1: IDH1 enzyme activity test in vitro IDH1 mutant catalyzes the NADPH-dependent reduction of α-KG (α-ketoglutaric acid) to 2-HG (2-hydroxyglutaric acid), and the consumed NADPH can be read out by fluorescence.

Reagents:

Basic reaction buffer: 50 mM $KH_2PO_4$, pH 7.5, 10 mM $MgCl_{12}$, 10% glycerol, 150 mM NaCl, 0.05% BSA (bovine serum albumin), 2 mM b-ME (2-mercaptoethanol), 0.003% Brij35 (oxyethylene lauryl ether)

Substrates and cCofactors:
IDH1 wt (wild type): 65 µM isocitrate ±50 µM NADP
IDH1 (R132H): 1500 µM α-KG ±15 µM NADPH
IDH1 (R132C): 500 µM α-KG ±15 µM NADPH Reaction Process:

1.33× enzyme (no control wells), buffer and NADP or NADPH (control wells) were added to the wells of a reaction plate. The compounds to be tested were dissolved in 100% DMSO, then added to the enzyme mixture (Echo550, nanoliter level) and incubated for 60 min after brief centrifugation. A mixture of 4× substrate and cofactor was added to start the reaction, briefly centrifuged, shaken, and incubated at room temperature for 45 min. A mixture of 3× lipoamide dehydrogenase and resazurin was prepared, added to the reaction solution to test the amount of the generated or remaining NADPH, incubated at room temperature for 10 min after simple centrifugation, and measured using a multifunctional microplate reader Envision (Ex/Em±535/590 nm).

Experimental results: as shown in Table 8 and Table 9:

TABLE 8

$IC_{50}$ results of in vitro enzymatic activity test on IDH1 (IDH1 R132H)

| Compound No. | Structure | IDH1 R132H (nM) |
|---|---|---|
| Compound represented by formula (I) | 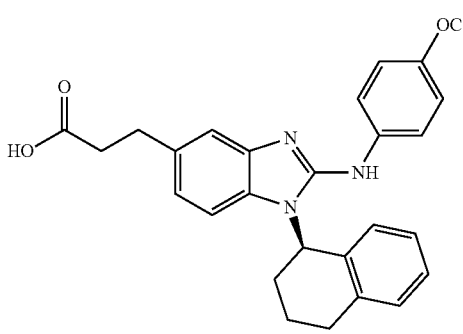 | 3.94 |

TABLE 9

| | | IDH1 R132C (nM) | IDH1 WT (nM) |
|---|---|---|---|
| Compound No. | Structure | | |
| Compound represented by formula (I) | | 12.79 | >10000 |

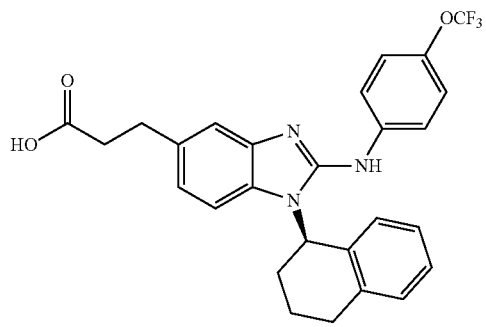 [SMILES: O=C(O)CCc1ccc2c(c1)nc(Nc1ccc(OC(F)(F)F)cc1)n2[C@@H]1CCCc2ccccc21]

Conclusion: The compound represented by formula (I) had a good inhibitory effect on the mutant IDH1R132H and IDH1R132C at the enzymatic level, and had no inhibitory effect on the wild-type IDH protein.

Experimental Example 2

IDH1 Cytological Activity Test

In this study, after co-incubating the compound with IDH1 mutant cell lines, the 2HG content in the cell culture supernatant was detected by LC-MS to determine the inhibitory activity of the compound on IDH1 mutants. IDH1 catalyzes the reduction of isocitrate to α-ketoglutaric acid (α-KG) in vivo, while IDH1 mutants further catalyze the reduction of α-KG to 2-hydroxyglutaric acid (2HG).

U87MG-IDH1-R132H cell line is a stable transfected cell line that can stably express IDH1-R132H mutant by transfecting U87MG cells with IDH1-R132H, and HT1080 cell line contains endogenous IDH1-R132C mutant.

The experimental process is as follows:

1) The compound was 3-fold serially diluted with DMSO and added to a cell culture plate, with a total of 10 concentrations, each concentration in duplicate. Negative control wells contained DMSO only, and positive control wells contained BAY1436032 at a final concentration of 5 µM. The final concentration of DMSO in all wells was 0.5%.

2) The IDH1 mutant cell line was seeded into the compound-containing cell culture plate at a density of 40,000 cells/well. Cells were co-incubated with compounds for 3 days in a 37° C., 5% $CO_2$ incubator.

3) After 3 days, 10 µl of cell culture supernatant was taken, diluted 21 times with 200 µl of dd$H_2$O to 210 µl and mixed well. 50 µl of the diluted solution was taken and added with 200 µl of a precipitant (acetonitrile containing 0.4 µg/ml D-2-hydroxyglutaric acid $^{13}C5$). After centrifugation at 4000 rpm for 10 min, 100 µl of the supernatant was taken to detect the content of 2-HG by LC-MS.

4) At the same time, the effects of the compound on the cell viability of IDH1 mutant cell lines was detected in parallel using the ATPlite 1Step kit according to the instructions.

5) The percentage inhibition (% inhibition rate) of IDH1 mutants by each concentration of the compound was calculated using the 2HG content data according to a formula of:

% Inhibition rate±(CPD−ZPE)/(HPE−ZPE)×100%;

and the percentage cytotoxicity (% cytotoxicity) of the compound against the IDH1 mutant cell line was calculated using the cell viability data according to a formula of:

% Cytotoxicity±(1−CPD/ZPE)×100%.

CPD: Signal value of compound wells
ZPE: Average signal of negative control wells, with 0.5% DMSO instead of compound
HPE: Average signal of positive control wells 6) The % inhibition rate and % cytotoxicity were fitted into a dose-response curve by the GraphPad Prism software to obtain the $IC_{50}$ value of the test compound.

The experimental results are shown in Table 10:

TABLE 10

IC$_{50}$ results of in vitro cell activity test of IDH1 (U87MG)

| Compound No. | Structure | U87MG IDH1-R132H (nM) |
|---|---|---|
| Compound represented by formula (I) | 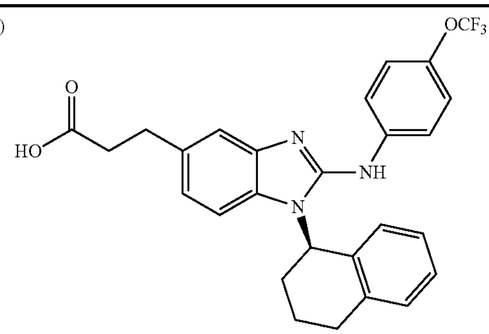 | 38.25 |

Conclusion: At the cellular level, the compound represented by formula (I) had a good 2-HG inhibitory effect on U87MG glioma cells with IDH1R132H mutation.

Experimental Example 3
Pharmacokinetic Evaluation in Mice

Experimental Purpose:

The pharmacokinetic parameters of the compound represented by formula (I) were detected in mice.

Experimental Program:

1) Experimental drug: compound represented by formula (I);

2) Experimental animals: 8 male CD-1 mice aged 7-10 weeks, divided into 2 groups, 4 mice in each group;

3) Drug preparation: for the tail vein injection group, an appropriate amount of the drug was weighed out and dissolved in a mixed solvent of DMSO: 20% hydroxypropyl beta-cyclodextrin (HPbCD)±10:90 to prepare a solution of 0.5 mg/mL; for the gavage administration group, an appropriate amount of the drug was weighed out and dissolved in a mixed solvent of DMSO: polyoxyethylene castor oil EL (Cremophor EL): 5% sulfobutylcyclodextrin (Captisol)±5: 10:85 to prepare into a suspension.

Experimental Procedure:

Animals in group 1 were given a single dose of 1 mg/kg drug at a concentration of 0.5 mg/mL via tail vein injection, and animals in group 2 were given the compound at a dose of 20 mg/kg at a concentration of 2 mg/mL by gavage. Animals were cross-collected for plasma samples at 0.0833 (the tail vein injection group only), 0.25, 0.5, 1, 2, 4, 6, 8 and 24 h after administration. The drug concentration in the plasma samples was determined by LC-MS/MS method, and the kinetic parameters of the tested drugs were obtained in Table 11:

TABLE 11

Pharmacokinetic evaluation parameters in mice

| Tail vein injection group | | | | |
|---|---|---|---|---|
| Clearance rate Cl (mL/min/kg) | Initial concentration C$_0$ (nM) | volume of distribution Vd (L/Kg) | Half-life T$_{1/2}$ (h) | Area under the curve AUC$_{0-last}$ (nM · h) |
| 2.17 | 3541 | 0.690 | 2.90 | 15463 |

TABLE 11-continued

Pharmacokinetic evaluation parameters in mice

| Gavage group administration | | | |
|---|---|---|---|
| Highest concentration C$_{max}$ (nM) | Time at highest concentration T$_{1/2}$ (h) | Area under the curve AUC$_{0-last}$ (nM · h) | Bioavailability F (%) |
| 33350 | 1.00 | 306609 | 99.1 |

Conclusion: The compound represented by formula (I) had good pharmacokinetic properties in mice.

The invention claimed is:

1. A crystalline form A of compound represented by formula (I), wherein its X-ray powder diffraction spectrum shows characteristic diffraction peaks at 2θ angles of 9.78±0.20°, 12.06±0.20° and 20.37±0.20°;

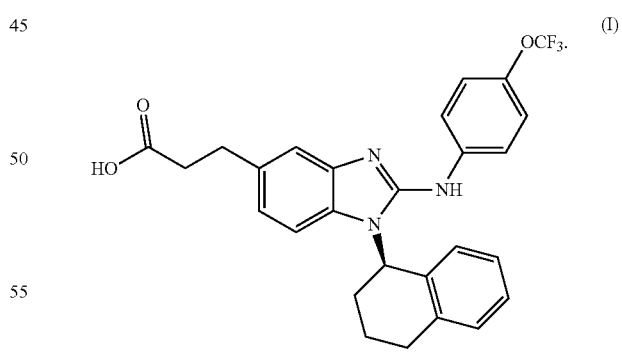

2. The crystalline form A according to claim 1, wherein its X-ray powder diffraction spectrum shows characteristic diffraction peaks at 2θ angles of 7.66±0.20°, 9.78±0.20°, 12.06±0.20°, 17.43±0.20°, 18.02±0.20°, 18.81±0.20°, 20.37±0.20° and 23.10±0.20°; or wherein its X-ray powder diffraction spectrum shows characteristic diffraction peaks at 2θ angles of 7.66±0.20°, 9.78±0.20°, 12.06±0.20°, 17.43±0.20°, 18.02±0.20°, 18.81±0.20°, 20.37±0.20°, 20.91±0.20°, 22.46±0.20° and 23.10±0.20°; or wherein its XRPD spectrum is shown in FIG. 1.

3. A crystalline form B of compound represented by formula (I), wherein its X-ray powder diffraction spectrum shows characteristic diffraction peaks at 2θ angles of 11.66±0.20°, 16.69±0.20° and 17.69±0.20°.

Figure 4:
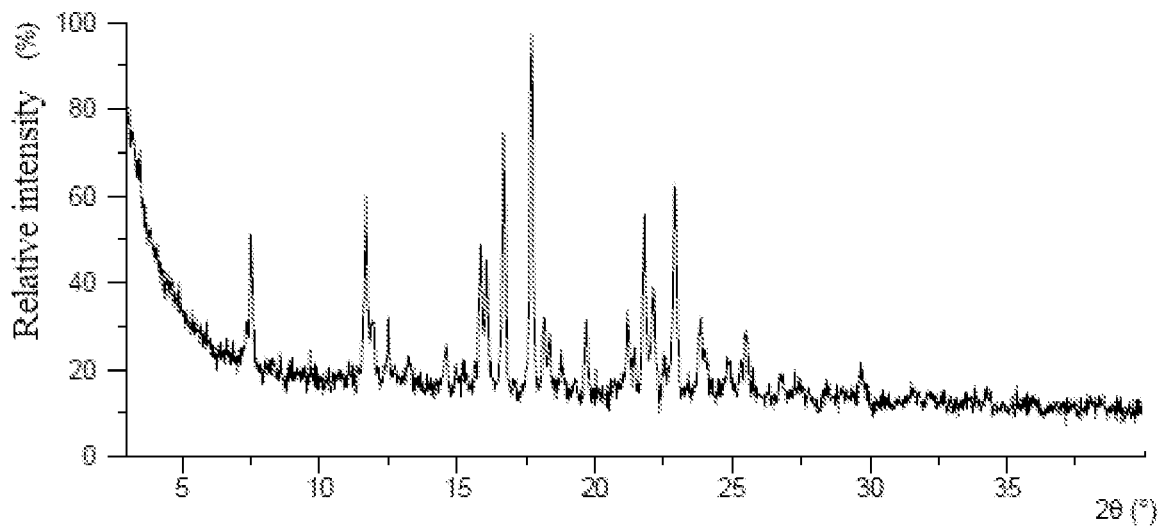
FIG. 4 is the Cu-Kα-radiated XRPD spectrum of the crystalline form B of compound represented by formula (I)

4. The crystalline form B according to claim 3, wherein its X-ray powder diffraction spectrum shows characteristic diffraction peaks at 2θ angles of 7.48±0.20°, 11.66±0.20°, 15.83±0.20°, 16.69±0.20°, 17.69±0.20°, 19.68±0.20°, 21.79±0.20° and 22.90±0.20°; or wherein its X-ray powder diffraction spectrum shows characteristic diffraction peaks at 2θ angles of 7.48±0.20°, 11.66±0.20°, 12.47±0.20°, 15.83±0.20°, 16.69±0.20°, 17.69±0.20°, 19.68±0.20°, 15.79±0.20°, 22.90±0.20° and 23.84±0.20°; or wherein its XRPD spectrum is shown in FIG. 4.

5. The crystalline form B according to claim 3, wherein its differential scanning calorimetry graph shows an endothermic peak at 246.8±3.0° C.

Figure 5:
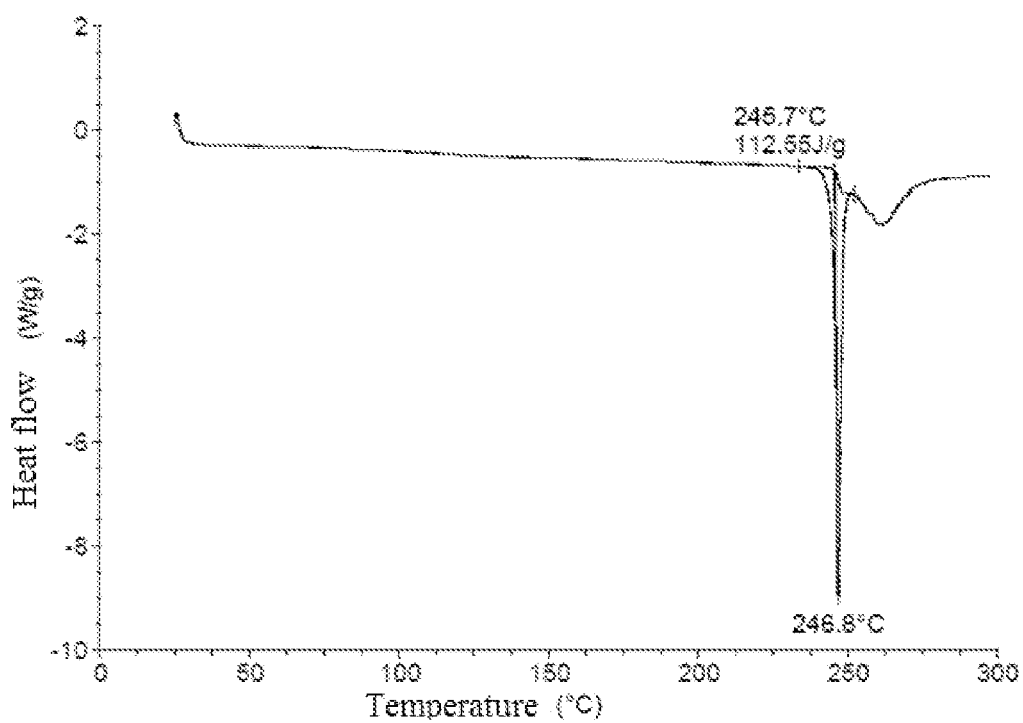
FIG. 5 is the DSC graph of the crystalline form B of compound represented by formula (I)

6. The crystalline form B according to claim 5, wherein its DSC graph is shown in FIG. 5.

7. The crystalline form B according to claim 3, wherein its thermogravimetric analysis graph shows a weight loss of 0.54% at 230.0° C.±3.0° C.

Figure 6:
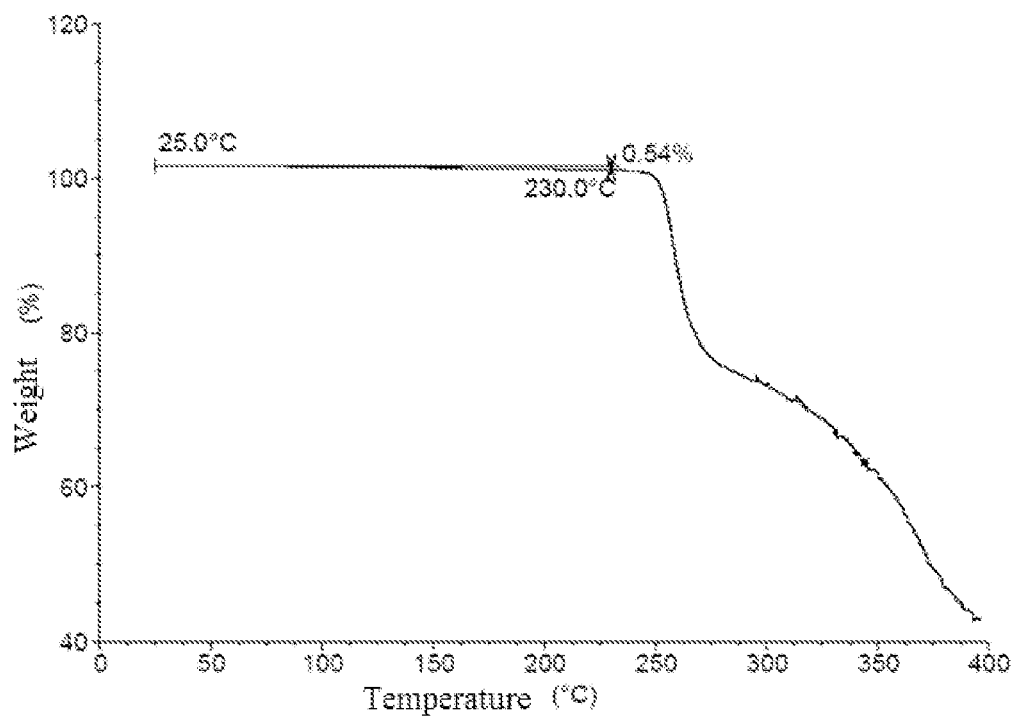
FIG. 6 is the TGA graph of the crystalline form B of compound represented by formula (I)

8. The crystalline form B according to claim 7, wherein its TGA graph is shown in FIG. 6.

9. A crystalline form C of compound represented by formula (I), wherein its X-ray powder diffraction spectrum shows characteristic diffraction peaks at 2θ angles of 9.59±0.20°, 18.19±0.20° and 19.74±0.20°.

Figure 7:
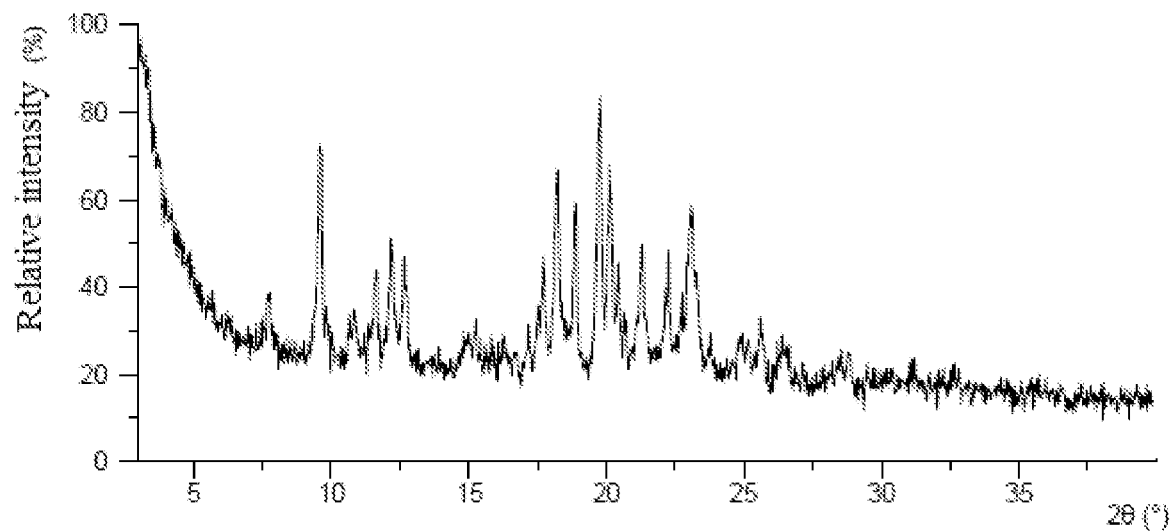
FIG. 7 is the Cu-Kα-radiated XRPD spectrum of the crystalline form C of compound represented by formula (I)
Figure 8:
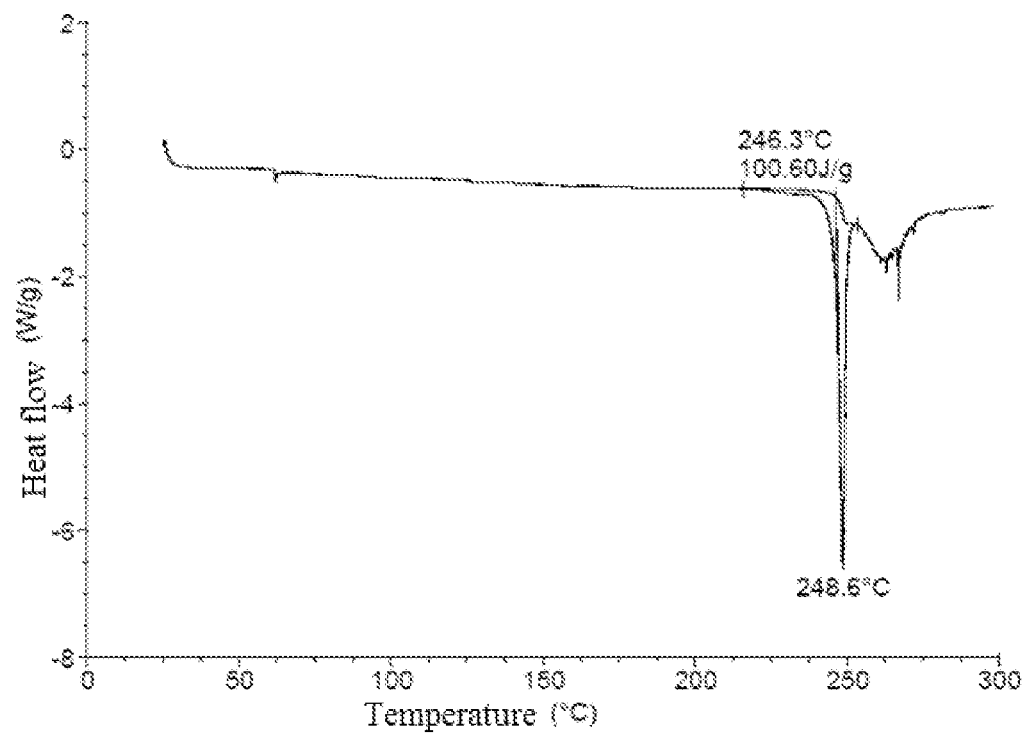
FIG. 8 is the DSC graph of the crystalline form C of compound represented by formula (I)
Figure 9:
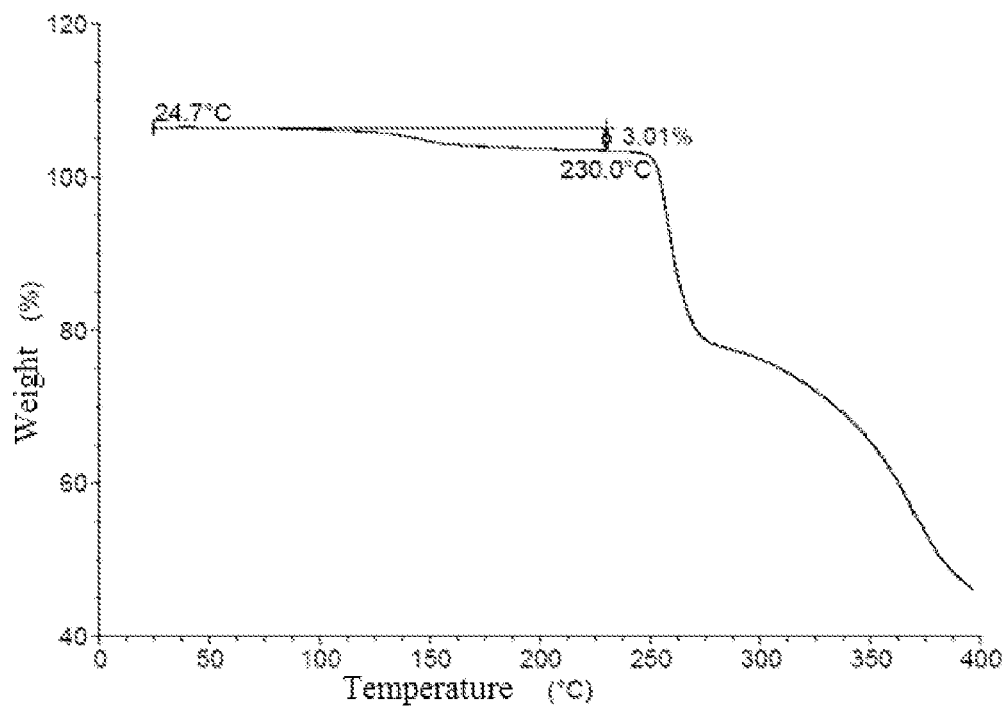
FIG. 9 is the TGA graph of the crystalline form C of compound represented by formula (I)

10. The crystalline form C according to claim 9, wherein its X-ray powder diffraction spectrum shows characteristic diffraction peaks at 2θ angles of 9.59±0.20°, 12.17±0.20°, 12.65±0.20°, 18.19±0.20°, 18.87±0.20°, 19.74±0.20°, 21.27±0.20° and 23.05±0.20°; or wherein its X-ray powder diffraction spectrum shows characteristic diffraction peaks at 2θ angles of 9.59±0.20°, 11.60±0.20°, 12.17±0.20°, 12.65±0.20°, 18.19±0.20°, 18.87±0.20°, 19.74±0.20°, 21.27±0.20°, 22.20±0.20° and 23.05±0.20°; or wherein its XRPD spectrum is shown in FIG. 7.

11. A compound represented by formula (II),

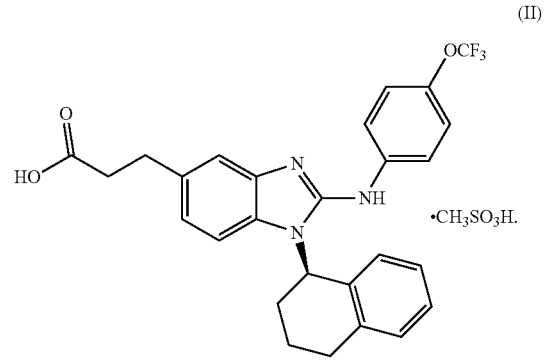

(II)

12. A crystalline form D of the compound represented by formula (II) according to claim 11, wherein its X-ray powder diffraction spectrum shows characteristic diffraction peaks at 2θ angles of 16.85°±0.20°, 19.93°±0.20° and 21.89°±0.20°.

13. The crystalline form D according to claim 12, wherein its X-ray powder diffraction spectrum shows characteristic diffraction peaks at 2θ angles of 7.31±0.20°, 8.48±0.20°, 13.08±0.20°, 16.85±0.20°, 17.44±0.20°, 19.93±0.20°, 21.89±0.20° and 22.49±0.20°.

14. The crystalline form D according to claim 13, wherein its X-ray powder diffraction spectrum shows characteristic diffraction peaks at 2θ angles of 7.31°, 8.48°, 13.08°, 14.64°, 16.85°, 17.44°, 19.93°, 21.89°, 22.49° and 25.87°.

Figure 10:
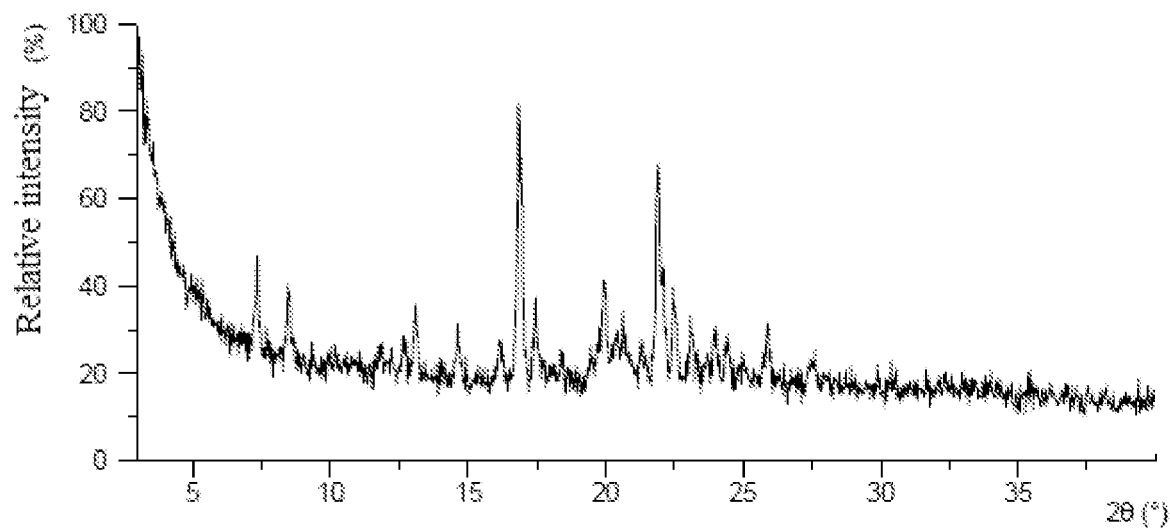
FIG. 10 is the Cu-Kα-radiated XRPD spectrum of the crystalline form D of compound represented by formula (II)
Figure 11:
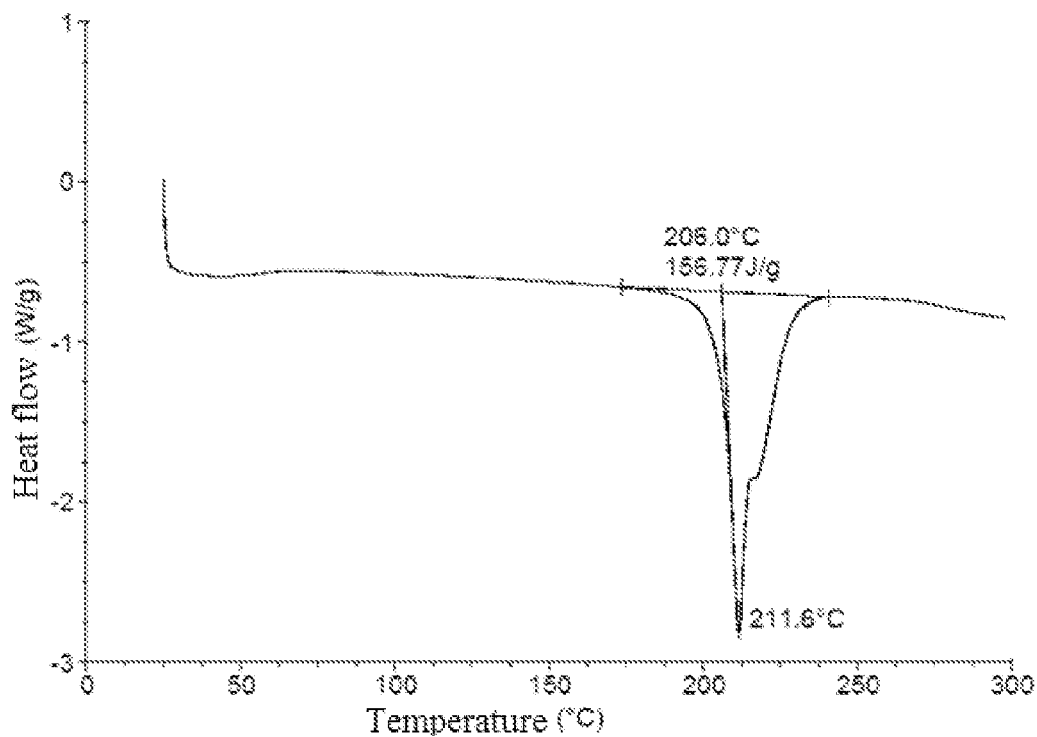
FIG. 11 is the DSC graph of the crystalline form D of compound represented by formula (II)
Figure 12:
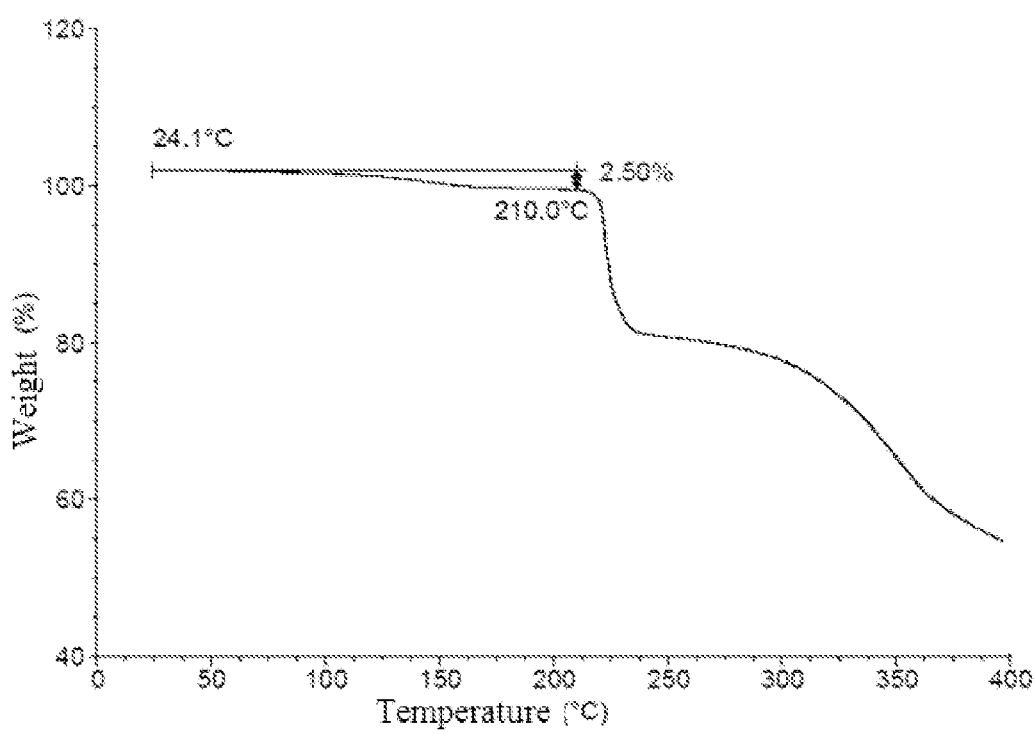
FIG. 12 is the TGA graph of the crystalline form D of compound represented by formula (II)
Figure 13:
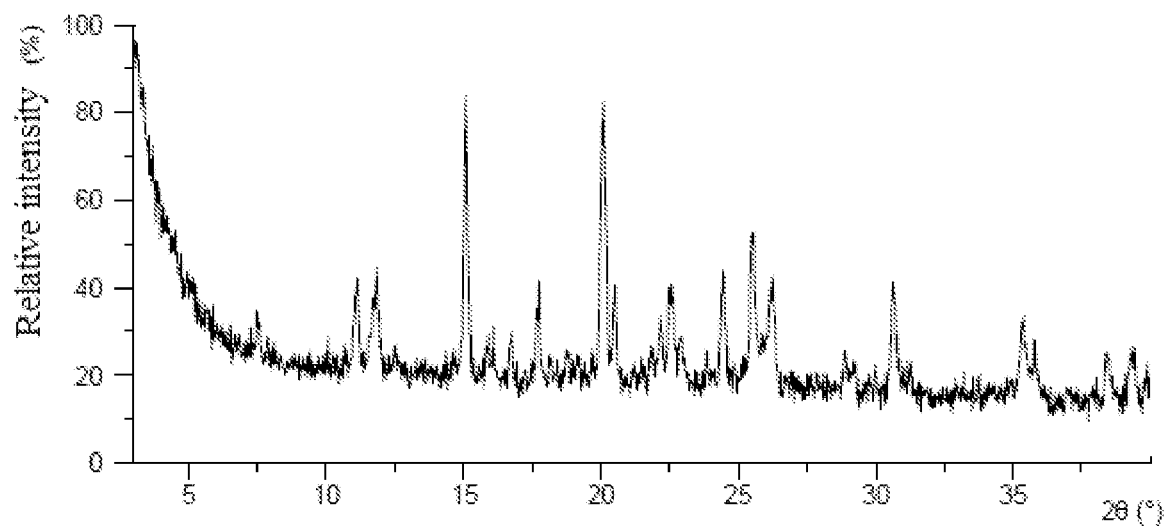
FIG. 13 is the Cu-Kα-radiated XRPD spectrum of the crystalline form E of compound represented by formula (III)
Figure 14:
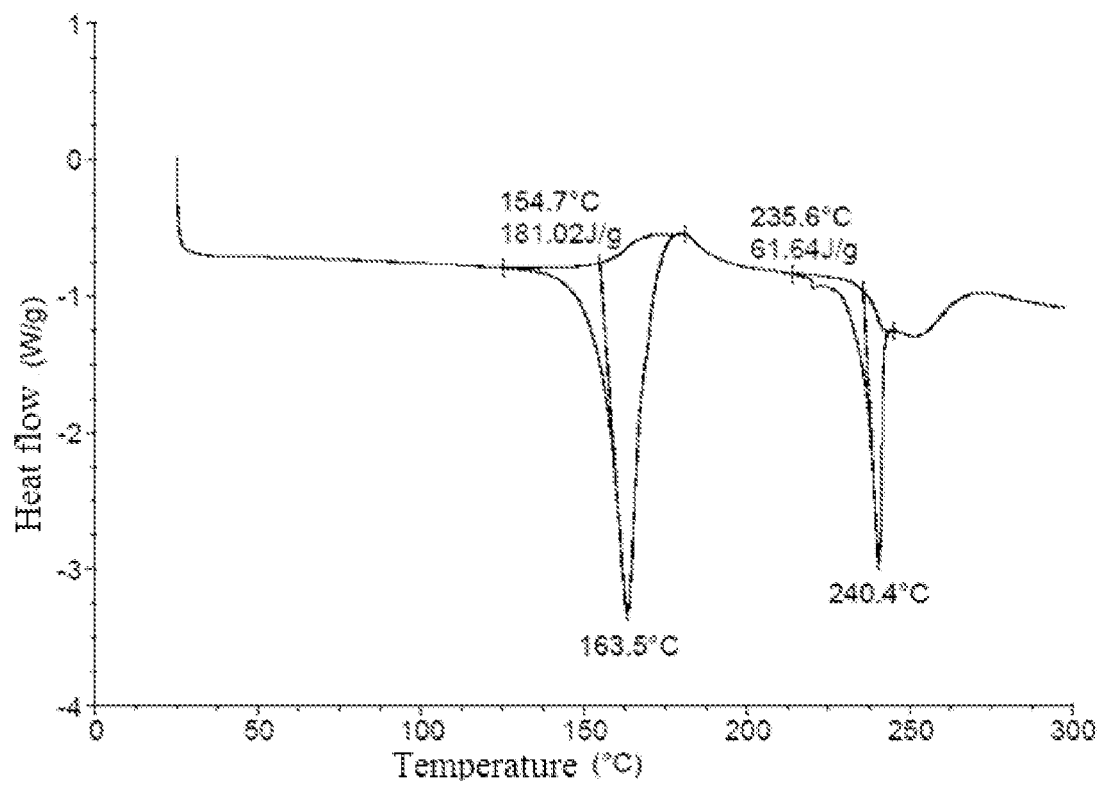
FIG. 14 is the DSC graph of the crystalline form E of compound represented by formula (III)
Figure 15:
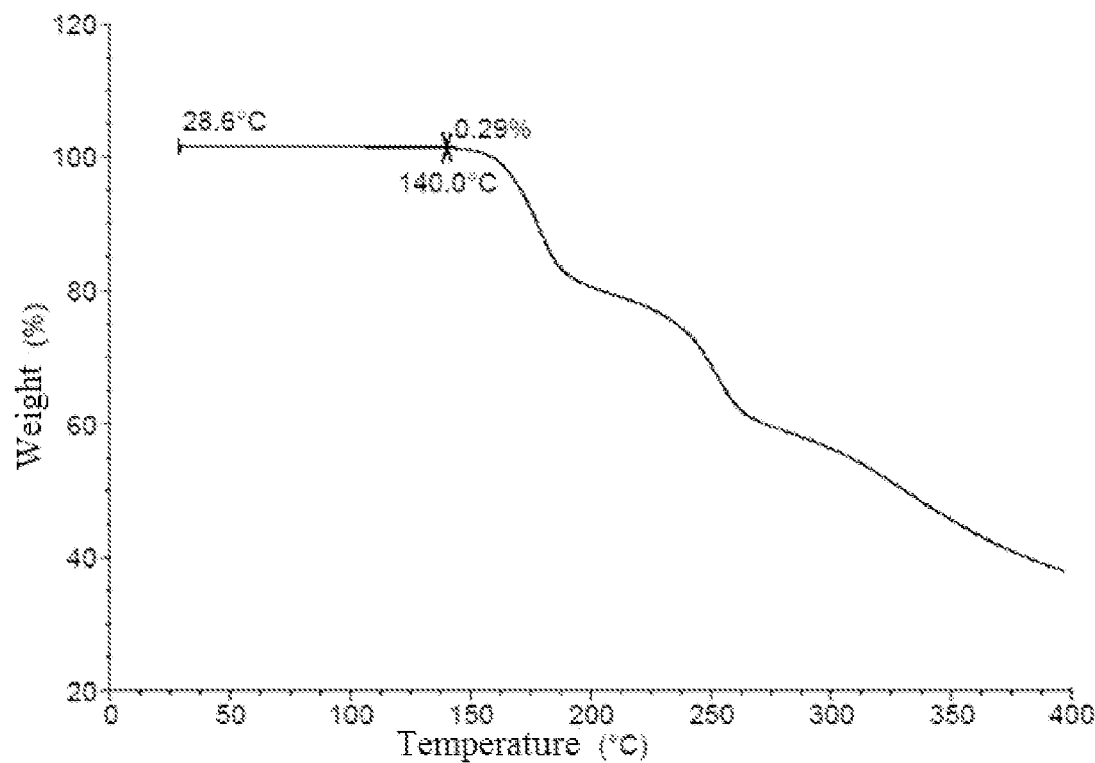
FIG. 15 is the TGA graph of the crystalline form E of compound represented by formula (III)
Figure 16:
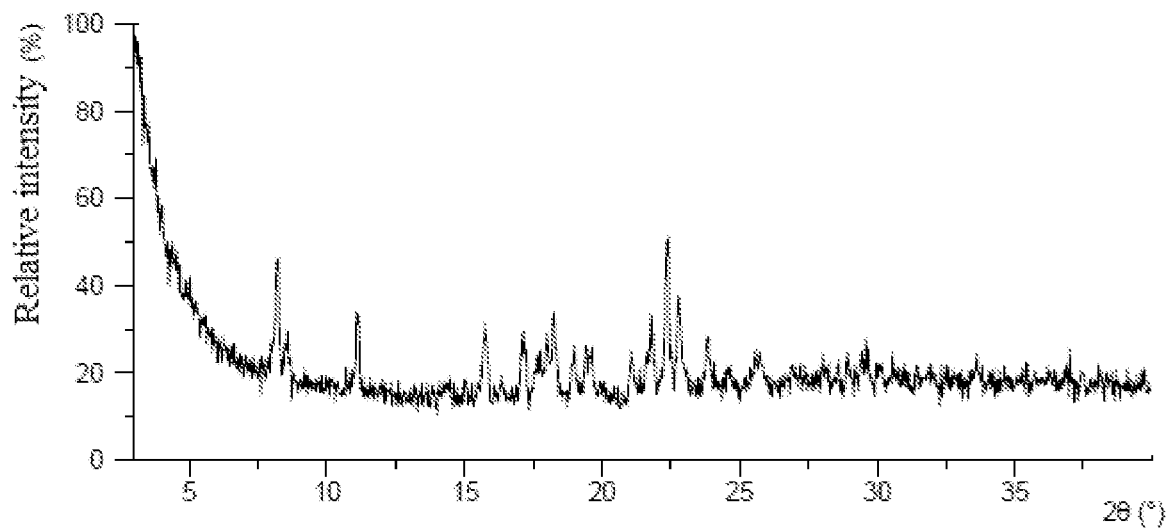
FIG. 16 is the Cu-Kα-radiated XRPD spectrum of the crystalline form F of compound represented by formula (IV)
Figure 17:
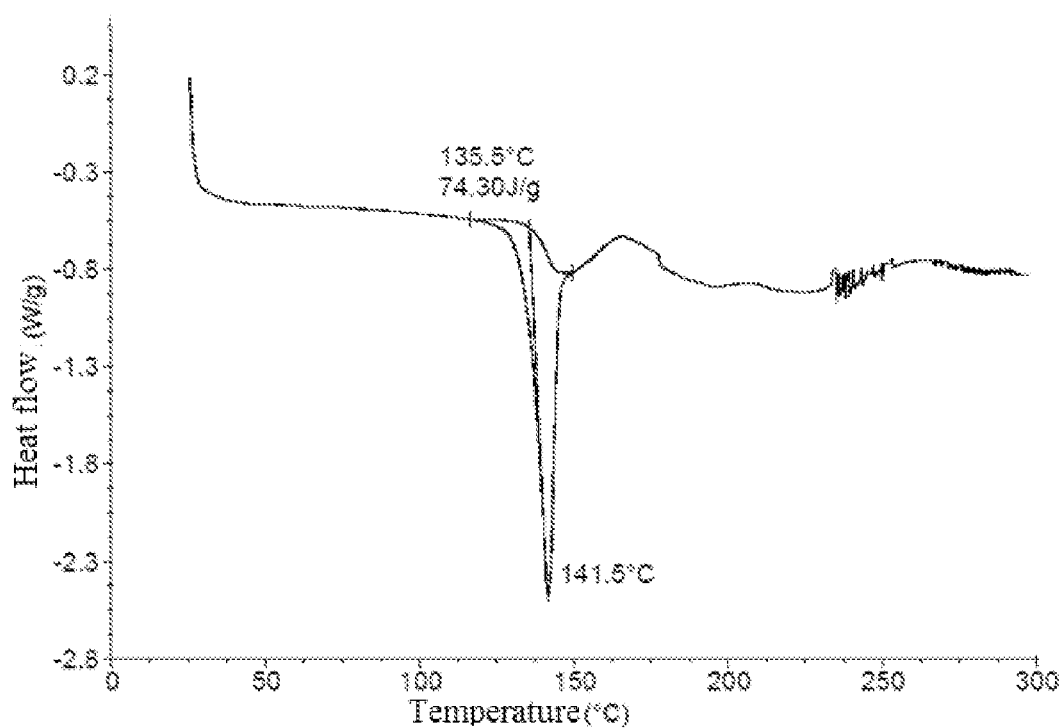
FIG. 17 is the DSC graph of the crystalline form F of compound represented by formula (IV)
Figure 18:
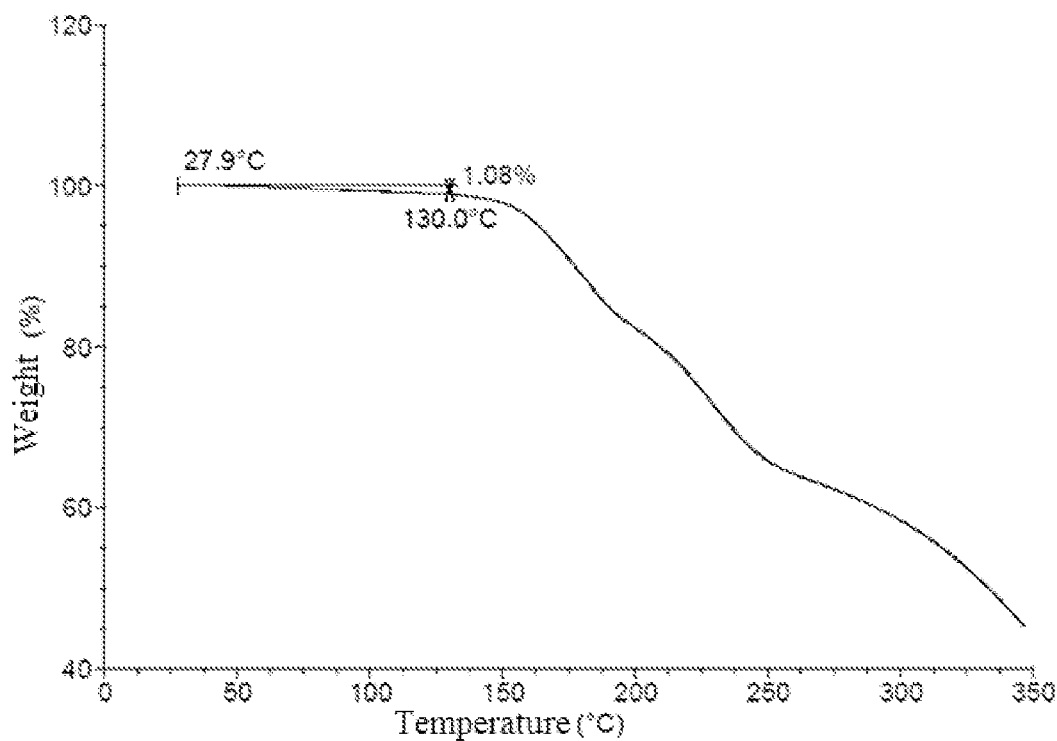
FIG. 18 is the TGA graph of the crystalline form F of compound represented by formula (IV)

15. The crystalline form D according to claim 14, wherein its XRPD spectrum is shown in FIG. 10.

16. A method for treating tumor in intrahepatic bile duct, comprising administering a therapeutically effective amount of the compound according to claim 11 to a subject in need thereof.

17. A method for treating tumor in intrahepatic bile duct, comprising administering a therapeutically effective amount of the crystalline form A according to claim 1 to a subject in need thereof.

18. A method for treating tumor in intrahepatic bile duct, comprising administering a therapeutically effective amount of the crystalline form B according to claim 3 to a subject in need thereof.

19. A method for treating tumor in intrahepatic bile duct, comprising administering a therapeutically effective amount of the crystalline form C according to claim 9 to a subject in need thereof.

20. A method for treating tumor in intrahepatic bile duct, comprising administering a therapeutically effective amount of the crystalline form D according to claim 12 to a subject in need thereof.

* * * * *